United States Patent
Shadduck

[19]

[11] Patent Number: 6,162,210
[45] Date of Patent: Dec. 19, 2000

[54] LASER MEDIATED TREATMENTS FOR PRESBYOPIA AND HYPEROPIA

[76] Inventor: John H. Shadduck, 1490 Vistazo West St., Tiburon, Calif. 94920

[21] Appl. No.: 09/174,366

[22] Filed: Oct. 15, 1998

[51] Int. Cl.[7] .................................. A61F 9/00; A61N 5/00
[52] U.S. Cl. ................................................... 606/5; 606/20
[58] Field of Search ................................ 606/4, 5, 6, 20, 606/21, 22, 23, 24; 604/21, 22, 23, 24

[56] References Cited

U.S. PATENT DOCUMENTS

| | | | |
|---|---|---|---|
| 4,820,264 | 4/1989 | Matsui et al. | 604/21 |
| 5,009,660 | 4/1991 | Clapham | 606/10 |
| 5,108,412 | 4/1992 | Krumeich et al. | 606/4 |
| 5,344,418 | 9/1994 | Ghaffari | 606/9 |
| 5,533,998 | 7/1996 | Freese et al. | 606/4 |
| 5,616,139 | 4/1997 | Okamoto | 606/4 |
| 5,741,245 | 4/1998 | Cozean et al. | 606/10 |
| 5,807,380 | 9/1998 | Dishler | 606/4 |
| 5,814,040 | 9/1998 | Nelson et al. | 606/9 |
| 5,843,071 | 12/1998 | Bath | 606/6 |

*Primary Examiner*—Sonya Harris-Ogugua

[57] ABSTRACT

A technique relating to orthokeratology for correcting presbyopic and hyperopic errors by means of a shallow-plane photo-microwelded intralamellar band. The technique is non-contact and is intended to be micro-invasive to allow its frequent repetition as a maintenance therapy. Non-contact photonic energy and a cyro-energy systems are provided in combination for creating an "inverse" thermal gradient in the anterior cornea. A computer-controlled spatial application system is provided for very high speed scanning of a photonic beam over the cornea. A "prosthetic" lens maintains the corneal surface in an optimal condition and prolate curvature. The lens-prosthesis further is adapted to mediate cryo- and photonic energies that propagate through the cornea to create the desired shallow-plane microweld effects.

18 Claims, 21 Drawing Sheets

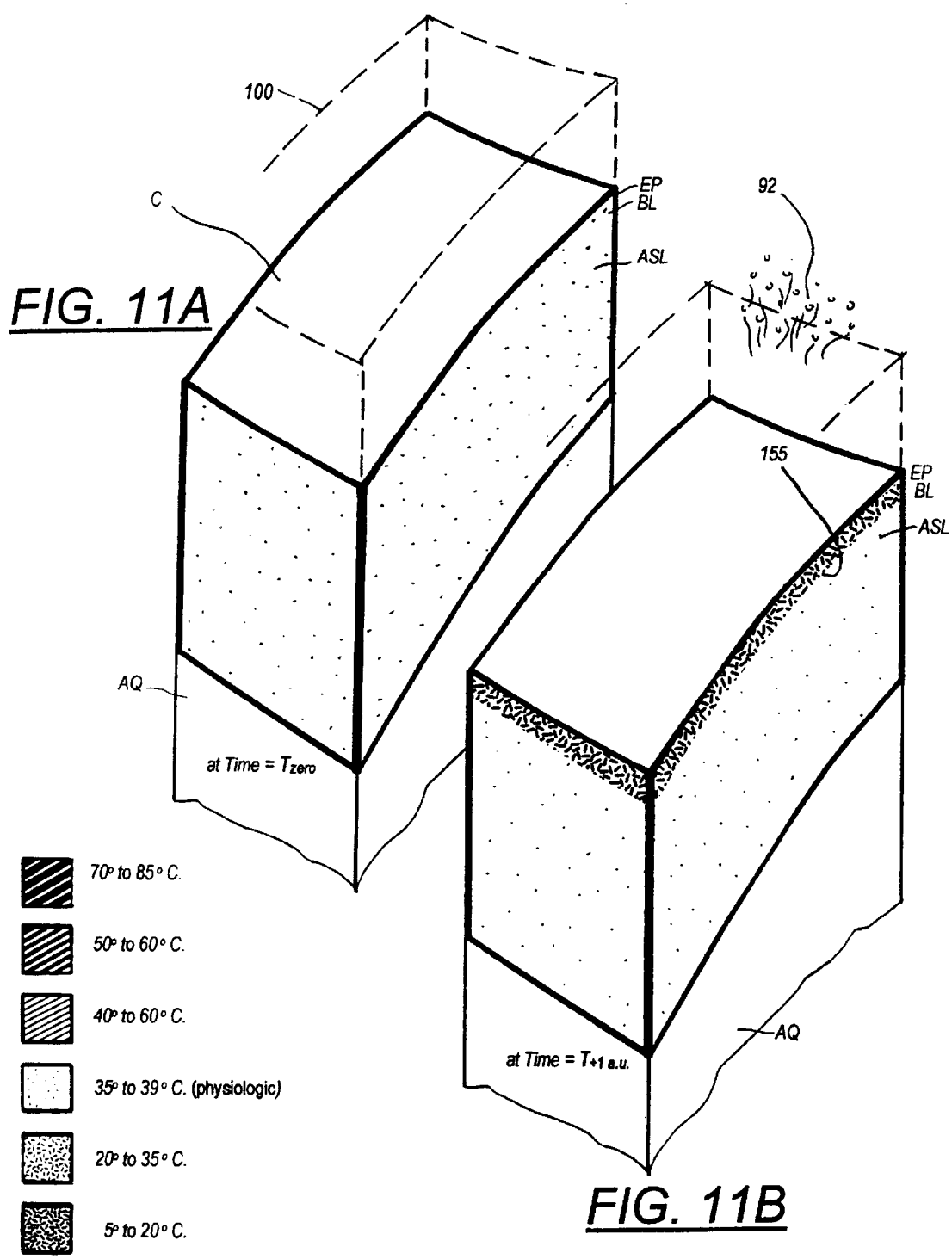

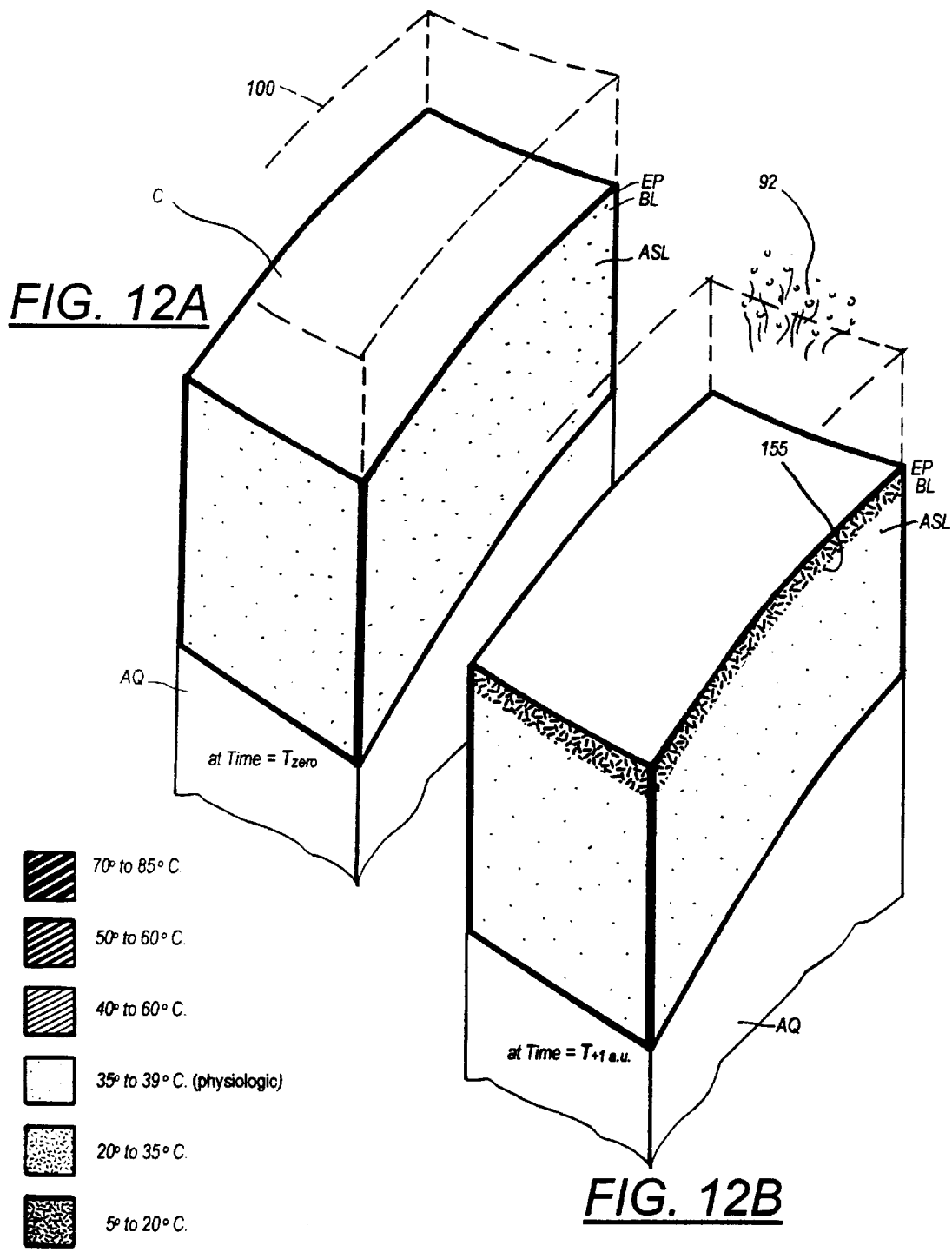

LASER MEDIATED TREATMENTS FOR PRESBYOPIA AND HYPEROPIA

BACKGROUND OF THE INVENTION

1. Field of the Invention

The present invention relates to ophthalmic devices and techniques and more particularly to an orthokeratology system for correcting presbyopic errors. An optical parametric oscillation converter (OPO) produces tunable-wavelength photonic energy that penetrates the cornea to create "shallow-plane" intra-lamellar microweld effects or intercalation of lamellae while a "prosthetic" lens maintains the corneal surface in a optimal condition and prolate curvature. The prosthetic lens is further adapted to mediate cryo- and photonic waves that propagate through the cornea to create the desired shallow-plane microweld effects—the novel technique and system described as a thermal-adjunct orthokeratology system (TAOS).

2. Description of the Related Art

The prior art methods of correcting refractive errors can be classified into three general categories: (1) external/internal appliances such as spectacles, contact lenses and intraocular lenses (IOL); (2) the practice of orthokeratology which uses progressively different-shaped contact lenses as prostheses to mold corneal curvature—followed by use of a retainer contact lens; (3) refractive surgeries of several types, which include various laser-based such as PRK LASIK and LTK; and keratoplasty procedures. The present inventive TAOS technique (thermal-adjunct orthokeratology system) disclosed herein and is a combination of orthokeratology and keratoplasty and utilizes two components: (i) a novel corneal prosthetic lens to mold and protect the anterior corneal condition and shape, and (ii) energy delivery systems for creating novel "shallow-plane" lamellar weld-effects that differ from other laser-based modalities (PRK, LASIK, LTK) both in "effect-depth" in the cornea and in the "effect-characteristics" of the photonics-cornea interaction. Further, the TAOS system and technique is unique in that it is being developed specifically to treat presbyopia. Prior art laser refractive surgical methods (e.g., LASIK and PRK;) are well-suited for treating myopia, but thus far are not proven for treating hyperopia, and are not used for treating presbyopia. Therefore, the TAOS presbyopia procedure is adapted to be a "micro-invasive" technique such that it can be used as a maintenance therapy to be performed repeatedly as the patient's presbyopic condition intensifies, and the treatment effects moderate.

As background, refractive errors result from the inability of the eye's optic system, consisting of the dome-shaped cornea C and the crystalline lens LE just behind it to properly focus images on the retina, the nerve layer at the back of the eye. Approximately 80 percent of the refracting power of a human eye is within the cornea; about 20 percent is within the lens LE (see FIG. 1A). Refractive errors generally include myopia, hyperopia, presbyopia and astigmatisms. Myopia is a refractive error that causes poor distance vision, and is characterized by an elongate eye or steepened corneal shape wherein images focused in front of the retina. Hyperopia is the opposite, and is caused by a shortened eye or flattened cornea that focuses images beyond the retina.

Presbyopia, the focus of this disclosure, results from the aging process and is caused by a diminished ability of the lens LE to elastically change its shape, generally which begins after about age 35 to 40.

The TAOS presbyopia and hyperopia treatment techniques disclosed herein deal with increasing the optical power of the cornea C to compensate for a decrease in the maximum power of lens LE. In other words, to overcome a lack of power in lens LE, the cornea's power must be increased by making its curvature more prolate (steeper in paracentral zone PZ) since it is not possible to precisely alter corneal radii. (see FIGS. 1B). As further background, four variables determine the refractive power of the cornea: (i) the optical power of the cornea in diopters; (ii) the optical power of the lens; (iii) the depth of the anterior chamber between the cornea and lens, and (iv) the axial length of the globe, i.e., distance of cornea and lens to retina. Each of the above factors may fall within a statistical "normal range" within standard deviations along a bell-curve, and the "correlation" among the four components can result in a minimal refractive error of 0.25 diopter or less (emmetropia). However, the four factors may still each be in a "normal range" but have an incorrect "correlation" and result in a refractive error (correlation ametropia), for example, needing correction of from 1.0 to 4.0 diopters. It is believed that about 90% of refractive errors relate to correlation ametropias of 4.0 diopters or less. The TAOS technique is directed specifically toward this population of refractive errors of 1.0 to 4.0 diopters.

To understand the techniques of the present invention in increasing the power of the cornea (steepening the cornea) in a maintenance therapy—and to understand the shortcomings of the prior art—it is necessary to describe (i) the distinct role played by the Bowman's layer BL and anterior stromal lamellae ASL in corneal morphology; (ii) the role of the tear film TF in photonic-cornea interactions.

As can be seen in the not-to-scale corneal section of FIG. 2, the cornea includes several distinct layers with indicated thicknesses. The anterior surface of the cornea consists of the epithelial layer EP and cornea C is not at all smooth and is made up of myriad projections and ridges called microvilli MV and microplicae MP. In order to allow the cornea to function and refract light, the corneal tear film TF which is repeatedly spread over the epithelium EP by the eyelids to provide the necessary smooth refracting surface. As shown in FIG. 2, the tear film This about 10–12 $\mu$m thick with an outermost lipid layer LIP that contacts the air and retards evaporation of the tear film. Whether a 12 $\mu$m tear film TF is intact, partly intact, entirely evaporated or purposefully removed can markedly change the depth of photonic energy absorption within the cornea.

The next layers below the tear film TF/epithelium EP are the Bowman's layer BL and the stroma S. The Bowman's layer BL is an acellular layer of randomly-oriented and overlapping collagen fibrils CF. (see FIG. 2). The stroma S constitutes about 85–90% of the corneal thickness. The entire stroma S is comprised of about two hundred lamellae L which lie in flat sheets and extend from limbus to limbus. Between the lamellae are keratocytes layers KL, the constitutive cells of the cornea which produce the intra-fibril ground substance GS and support synthesis of collagen fibrils CF (see FIG. 3).

The Bowman's layer is from 15 $\mu$m to 20 $\mu$m thick and blends posteriorly into the stroma S, or more particularly into the anterior stromal lamellae ASL (see FIG. 3). For the purposes of this disclosure, the stromal lamellae are divided into three regions: the anterior stromal lamellae ASL; medial stromal lamellae MSL; and the posterior stromal lamellae PSL. In general, each lamella (sheet) consists of strong parallel collagen fibrils CF maintained in a spaced separation by ground substance GS. In the posterior stromal lamellae PSL, the collagen fibrils CF run at approximately "right angles" from one lamellae L to the next, and such posterior lamellae are distinct and non-interlocking. In contrast to the posterior lamellae PSL, the anterior stomal lamellae ASL have collagen fibrils CF are oriented at oblique angles, lamellae-to-lamellae. Further, the collagen fibrils CF of the anterior lamellae ASL interleave between over- and underlying lamellae. In other words, the most anterior lamellae ASL are interlocked to a significant extent and thus act similar to the Bowman's layer BL in which collagen fibrils are random and overlap. Such interleaving of fibrils in the anterior lamellae ASL can easily be seen in the anterior ¼ to ⅓ of the stroma S (the ASL herein) as the layer appears gray-like in slit lamp microscopy.

It is believed that the Bowman's layer BL and the anterior stromal lamellae ASL, due to the interweaving of the collagen fibrils CF and the oblique cross-orientation of the fibrils, are the most important elements in maintaining the anterior corneal curvature in the "normal range" (±7.7 mm radius). FIG. 3 shows the intercalation of the Bowman's layer BL and the anterior lamellae ASL, where the random collagen fibrils project into and entwine with the more layered ordering of stromal collagen fibrils. The Bowman's layer BL and anterior stromal lamellae ASL are unyielding to stretching forces and thus are adapted to contain the substantial intraocular pressure (IOP) of the eye. The TAOS technique disclosed herein of creating shallow-layer weld-effects focuses on these layers to create intercalations thereof, and therefore from time-to-time the layers will be referred to herein as the Bowman's+ASL region of the stroma S. Such unyielding characteristics of the Bowman's+ASL is evident in all cases of corneal swelling (e.g., stromal edema or prior art photonic interactions in the mid-stroma and posterior stroma) which causes the cornea to protrude severely posteriorly since the above-described lamellar interleaving or interdigitation is lacking poteriorly.

The prior art LTK method differs markedly from the TAOS technique disclosed herein when comparing the "effect-characteristics" at depths in the cornea. The stated objective of the prior art LTK method is to create so-called "shrinkage" of collagen fibrils into clumps in a series of spots around the cornea to create lines of tension between the spots to affect corneal curvature. The so-called "shrinkage" of corneal collagen fibrils occurs at from about 55°–60° C. (see Stringer, H., Parr, J., "Shrinkage Temperature of Eye Collagen", *Nature* 1964; 204:1307.; see also U.S. Pat. No. 4,976,709). The TAOS technique disclosed herein utilizes higher temperatures to cause the desired microweld-effects which cause fusions of, or lesions within, a lamellar region as described below.

What is needed is a non-contact photonics system for re-shaping corneal curvature (i) that provides a minimally invasive therapy, (ii) that causes minimal thermal insults to cornea, both in duration of exposure and the volume of tissue affected; (iii) that treats the most widespread refractive disorders, the first being presbyopia and the second being hyperopia, (iv) that provides a solution that is not dependent on transient lines-of-stress within the stroma (v) that reduces regression of effects; (v) that protects the epithelial layers from damage, (vi) that provides energy delivery systems that are highly individualizable for irregular or astigmatic corneas to reach the greatest number of candidates, and (vii) that provides a repeatable maintenance therapy to accommodate natural presbyopic age-effects of the patient's lens over his or her lifetime.

SUMMARY OF THE INVENTION

The present invention provides techniques and photonic and cryo-energy delivery systems for non-ablative corneal remodeling for correction of presbyopia and hyperopia. In order to correct such presbyopia and hyperopia, the technique is adapted to make the anterior curvature of the patient's cornea prolate, with a steepened paracentral zone PZ, which will focus images on the retina instead of beyond the retina. The paracentral zone is defined herein as the region about the optical axis of the cornea having an inner diameter of about 4 mm. and an outer diameter of about 10 mm. (see FIG. 4A).

The techniques and systems are herein termed thermal-adjunct orthokeratology systems (TAOS), which accurately describes key aspects of the novel refractive approach. Conventional orthokeratology describes a "prosthetic molding" approach for correcting refractive disorders. In orthokeratology, the patient's cornea is fitted with a series of progressively different shaped contact lens-type prostheses which will mold the curvature of the cornea.

In the TAOS technique, the thermal-adjunct aspect of the orthokeratologic or prosthetic molding approach combines the use of photonic and cryo-energy delivery systems to perform shallow layer micro-welding or photo-intercalation of anterior stromal lamellae, at the same time a lens-prosthesis maintains corneal curvature in a desired prolate shape (or preferably a somewhat overcorrected prolate shape which will be described below). The shallow layer micro-welding, when created in a "360° band" in the anteriormost stroma around the entire paracentral zone PZ of the cornea, can flatten the zone and provide a paracentral cinch around the cornea to induce and maintain the prolate corneal curvature, approximating the shape of the lens-prosthesis. As can be seen in FIG. 4A, the pre-treatment corneal curvature is more or less spherical having a circumference CIR in the center of paracentral zone PZ. FIG. 4B shows a micro-welded "band" (indicated as BAND in the Figures) in the center of paracentral zone PZ to maintain the cornea in a prolate shape. In FIG. 14B, it can be seen that circumference CIR' caused by the micro-welded band serves as a circumferential cinch to maintain the cornea in the slightly prolate shape (Cf. CIR in FIG. 14A). As described below, besides maintaining the cornea in a prolate shape during treatment, the lens-prosthesis protects the condition of the anterior corneal surface during energy deliveries, which includes thermal shocks from cryogenic cooling and photonic heating.

In order to accomplish the above-described shallow-layer photo-microwelding, several novel systems are required, the most important systems adapted (i) to create an "inverse thermal gradient" in the cornea during the microseconds or less required for photo-microwelding at a subsurface depth while maintaining the epithelium EP at physiologic temperature, and (ii) to scan multiple photonic energy beams over the anterior surface of the cornea in opposing quadrants of the paracentral zone PZ to create the "360° band".

In recent years, research has progressed on the use of lasers in the broad field of "tissue-welding". The exact binding mechanism of such tissue welding or fusion is still somewhat unclear, but the majority of researchers agree that proteins in tissue (e.g., collagen) play the major role in tissue fusion, when such proteins thermally denature and thereafter renature into a fused-together volume (see, e.g., Cilesiz, I., Thomsen, S., Welsh., A. J., "Controlled Temperature Tissue Fusion: Argon Laser Welding", *Lasers in Surg. & Med.* 21:269–277 (1997); Killkelly, F. X., et al., "Tendon Repair by Laser Welding", *Lasers in Surg. & Med.* 19:487–491 (1996)).

In this disclosure, the technique of creating corneal lamellar micro-welds is a novel subset in the field of such tissue welding. More specifically, the photonic-tissue interaction proposed herein may be best described as a photo-intercalation modality that intercalates stromal procollagen fibers caused by the denaturation-and-renaturation process. The term intercalation is commonly used to describe the insertion or projection of collagen fibrils into under- and overlying layers between the Bowman's layer BL and adjacent anterior stroma ASL. An objective or the invention is thus to create such a photo-intercalation effect with nascent collagen fibrils in the anterior stroma ASL region, which can maintain the cornea in a prolate shape. In this disclosure, the terms photo-microwelding technique and photo-intercalation modality may be used interchangeably to describe the technique of invention. It should be appreciated, however, that the photo-microwelding technique based on the creation of an "inverse" thermal gradient may apply to any body tissues, whereas the term photo-intercalation modality more particularly describes the objective as it relates to the denaturation-and-renaturation process in a corneal lamellae for refractive purposes.

The photo-intercalation of procollagen fibers in the cornea is accomplished in a range between about 70° to 85° C. In this photo-intercalation modality, the stromal cellular and protein constituents, comprising tropocollagen molecules, GAGS, keratocytes, and other proteins (plus water), are denatured and thus intermixed at the instant of the photonic energy absorption. Upon cooling, renaturation of the affected volume creates the "melding" or "welding" of such constituents, which along with dehydration, will create the tightened band to flatten the paracentral zone PZ resulting in a more prolate anterior corneal surface. As described next, the anterior surface overlying the photo-intercalated region is substantially prevented from "bulging" anteriorly by the lens-prosthesis.

The photo-intercalation modality disclosed herein is accomplished at a higher temperature point than the prior art laser thermal keratoplasty (LTK) methods that propose collagen "shrinkage" temperature levels (55°–60° C.). What is more important is the fact that the photo-intercalation modality of the present invention causes a refractive change in the cornea by entirely differently means than the prior art LTK methods. The technique of the invention creates a photo-microwelded band in 360° around the paracentral zone PZ to cinch the cornea, whereas the prior art LTK methods create lines-of-stress between amorphous-clumped collagen fibrils AFC in the mid-stroma (see FIG. 13B).

The TAOS technique of the invention is accomplished with a corneal lens-prosthesis in place which serves multiple therapeutic purposes.

(i) maintaining the anterior cornea surface in a desired form, both locally flat over the region of the photo-intercalation band and globally curved at a particular radii or prolate curvature, (ii) protecting the epithelium from damage from thermal shock associated with photonic energy delivery, and (iii) mediating the cryo-shock effects of the cooling wave that propagates through the epithelium EP and stroma S.

Underlying the development of the TAOS technique were several paramount considerations. Common to all prior art forms of thermal remodeling of the cornea were excessive thermal effects, (i) in the volume of corneal tissue affected, and (ii) in the duration of photonic energy delivery. It is believed that such excessive thermal insults to the 500 micron thick cornea directly resulted in the numerous shortcomings of prior art procedures (epithelial damage, regression of effects, endothelial bulging and damage, corneal thinning among others). Therefore, the objectives of the TAOS procedure included reducing by several orders of magnitude (i) the extent, and (ii) the duration of thermal effects delivered intra-stromally, when compared to the prior art laser thermal keratoplasty (LTK) methods.

In a TAOS procedure, the objective is to limit the photo-intercalation effects to a very shallow layer, e.g., from 50 to 150 microns in depth or about 10%–15% of the thickness of the cornea. In the prior art laser thermal kerotoplasty, the thermal effects extend entirely through the 500–550 micron thickness of the stroma.

Concerning stromal volume, in a TAOS procedure, the predicted tissue volume that is targeted for "treatment" is less than about 5% of the volume affected in prior art thermal keratoplasty (LTK). In the TAOS technique, only a thin band of anterior stromal tissue is remodeled or photo-intercalated. In contrast, the prior art laser thermal keratoplasty techniques create sixteen or more full corneal-thickness volumes of stromal "shrinkage", which in turn create lines-of-stress across the cornea.

In terms of limiting the duration of temperature-effects, the TAOS technique limits the duration of photonic interaction to between about 50 ns and 300 ms to cause photo-intercalations in the anterior stroma only, which is believed to be about 10% of the duration of laser energy delivery in prior art (LTK) laser keratoplasty. Beyond the fact that the TAOS procedure is accomplished in such fractions of a second, the TAOS cryo-energy delivery system reverses any residual thermal effects within microseconds following photonic energy delivery—thus instantly returning the cornea entirely to physiologic temperature (or lower).

In this regard, the parameters of the photo-intercalation modality can be seen in Chart A when compared to temperature ranges and the attendant effects on collagen-containing tissues. Chart A illustrates that below about 55° C., there are no significant effects on collagenous tissues, except for dehydration and the cell death (e.g., in the cornea, keratocyte deaths). At about 55° to 60° C., as described by Stringer and Parr in their 1964 investigations, the collagen "shrinkage" modality proposed in laser thermal keratoplasty (LTK) is shown wherein cross-links within the procollagen fibers' triple-helix domain are reduced resulting in so-called tissue "shrinkage". At a temperature range of about 70° to 85° C., the photo-intercalation modality is shown in which tropocollagen molecules and other proteins are entirely denatured, intermixed and thereafter renatured which results in nascent collagen fibrils forming the desired intercalation. Beyond the photo-intercalation modality proposed herein, for example at 100°–200° C., the photo-disruption or vaporization modality is shown, wherein high-energy photons will explosively disrupt the chemical structure of molecules resulting in vaporization or ablation.

CHART B

| | 35°–39° C. (physiologic) | 44° C. | collagen "shrinkage" modality 55°–60° C. | photo-intercalation modality 70°–85° C. | photo-disruption modality 100°–200°+ C. |
|---|---|---|---|---|---|
| EFFECTS IN TISSUE | none | cell death begins | tissue shrinkage, cross-link dissociation molecular helical domain | denaturation/renaturation, tissue welding, coagulation | tissue cutting, vaporization of cellular contents, tissue ablation |
| LASER, OTHER DEVICE TO CAUSE EFFECTS IN TISSUE | | | laser, Rf current flow, microwave, themophore | laser, Rf electrode, themophore | high-energy laser, intense arc from mono-polar electrode |

In practicing the technique of the invention, the cryo-dosimetry system pre-cools the cornea by spraying a tiny predetermined dose of bio-inert cyro-spray on the lens prosthesis over the cornea. From about 1.0 to 500.0 ms following initiation of cryo-spray delivery, the photo-dosimetry controller triggers photonic energy delivery. In this sequence of cyro- and photonic energy delivery, a cyro-wave first propagates through the cornea at velocity $V_{CW}$, which is slow in comparison to the velocity of photon beam propagation $V_P$. This disparity is exploited to create a true "inverse" thermal gradient in the anterior layers of the cornea to allow photo-microwelding or photo-intercalation of anterior stromal lamellae. While cryo-wave is propagating through the cornea, the photonic energy beams are scanned along pre-selected paracentral zone paths over the lens-prosthesis and cornea. Since $V_P$ is significantly greater than $V_{CW}$, the photon beams can be timed to "overtake" the cryo-wavefront at a particular depth within the anterior stromal lamellae. Thus, an "inverse" thermal gradient exists for an instant (ns to ms) when the photonic energy is absorbed and is extinguished in advance of the cryo-wave. Such photonic energy is absorbed in front of the cryo-wave and heats the targeted volume instantly in a period ranging from femto- to pico-seconds to create the photo-microweld. At the same time, the photonic energy absorbed behind the cryo-wave warms the cooled anterior surface layers back to near-physiologic temperatures. During the practice of this technique, the prolate shaped lens-prosthesis, besides maintaining the corneal shape and condition, mediates the shock of cryo-spray boiling off the prosthesis surface.

In general, the present invention advantageously provides a technique of creating an inverse thermal gradient in tissue to allow a subsurface temperature of about 70°–85° C. to microweld tissue while overlying surface tissue is maintained at physiologic temperature of about 35°–39° C.

The invention provides a technique for creating a 360° microwelded intralamellar band around the cornea to make the cornea prolate as means of increasing optical power to correct presbyopic and hyperopic conditions.

The invention provides a technique that utilizes a lens-prosthesis to both mediate energy shocks to the cornea and to mold the cornea during the photo-microweld treatment The invention advantageously provides a technique that elevates in temperature only a very limited volume of corneal tissue thus not causing significant cell death in keratocyte layers in the cornea which it is believed will reduce the wound healing response and associated regression of effects.

The invention provides a device which includes a tuneable wavelength source of photonic energy for controlling the depth of photon absorption and thus the depth of the microweld.

Additional features and advantages of the device and method of the present invention will be understood from the following description of the preferred embodiments, which description should be taken in conjunction with the accompanying drawings.

BRIEF DESCRIPTION OF THE DRAWINGS

FIGS. 11A–11E are a sequence of views extending over arbitrary units (a.u.) of time in ns or microseconds showing a cryo-wave propagating through the cornea and the temperature gradients thereby created at a.u. time intervals; FIG. 11A depicting the corneal volume at physiologic temperature; FIG. 11B depicting a cryo-spray reducing the anterior surface temperature of the corneal volume; FIG. 11C depicting the cryo-wavefront traversing the mid-stroma; FIG. 11D depicting the cryo-wavefront traversing the entire cornea; and FIG. 11E depicting a corneal volume returning toward physiologic temperature.

FIGS. 12A–12E are a sequence of views illustrating a manner of practicing the technique of the invention, with the views extending over arbitrary units of time (milliseconds) showing tissue temperatures as the combination of cryo-wave propagation and photonic beam penetration within the cornea; FIG. 12A again depicting the corneal volume at physiologic temperature; FIG. 12B depicting a cryo-spray reducing the anterior corneal surface temperature; FIG. 12C depicting the cryo-wavefront traversing the cornea and the photonic beam overtaking the cryo-wavefront to create a photo-microweld in advance of the cryo-wavefront; FIG. 12D depicting the cryo-wavefront then cooling the photo-microwelded region; and FIG. 12E depicting a corneal volume returning toward physiologic temperature.

DETAILED DESCRIPTION OF THE INVENTION

Figure 1A:
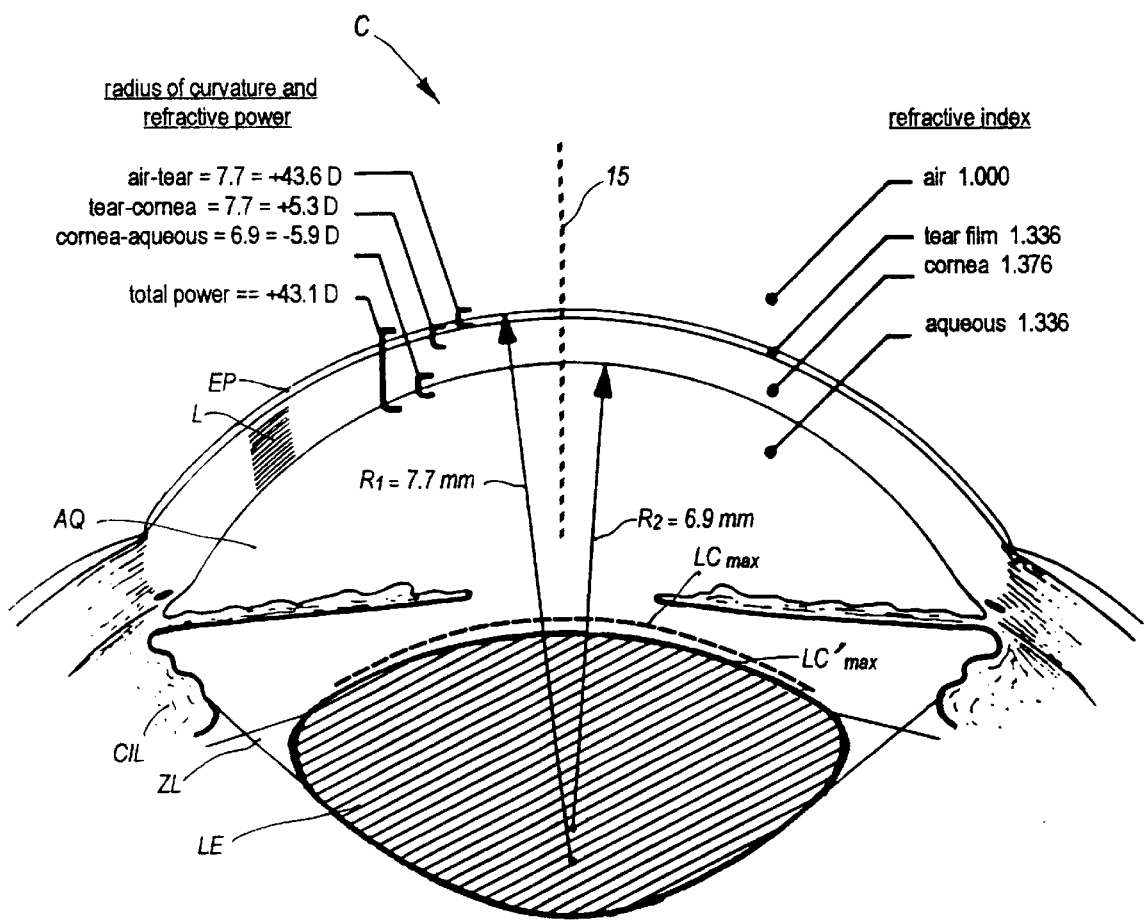
FIG. 1A is a sectional view of the cornea and lens of a patient's eye showing anatomic structures as well as indices of refraction of the various structures.
Figure 1B:
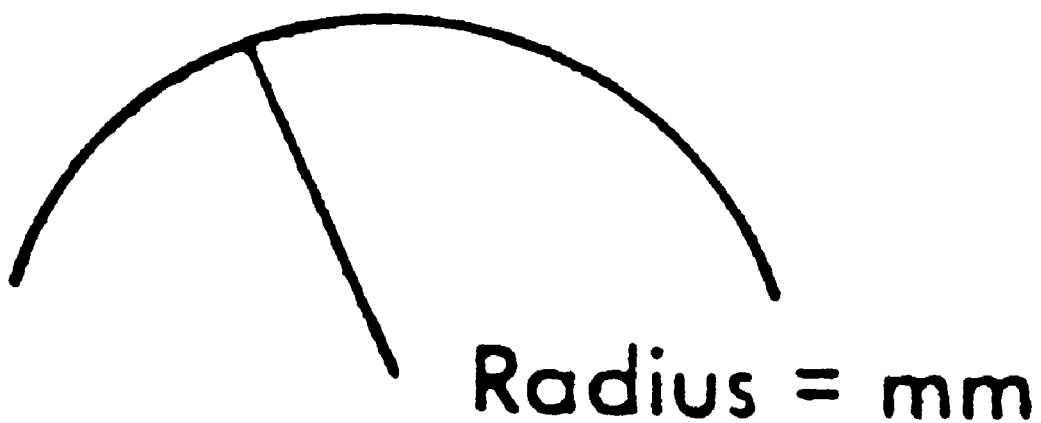
FIG. 1B is an illustration of corneal anterior which relates to optical power.
Figure 2:
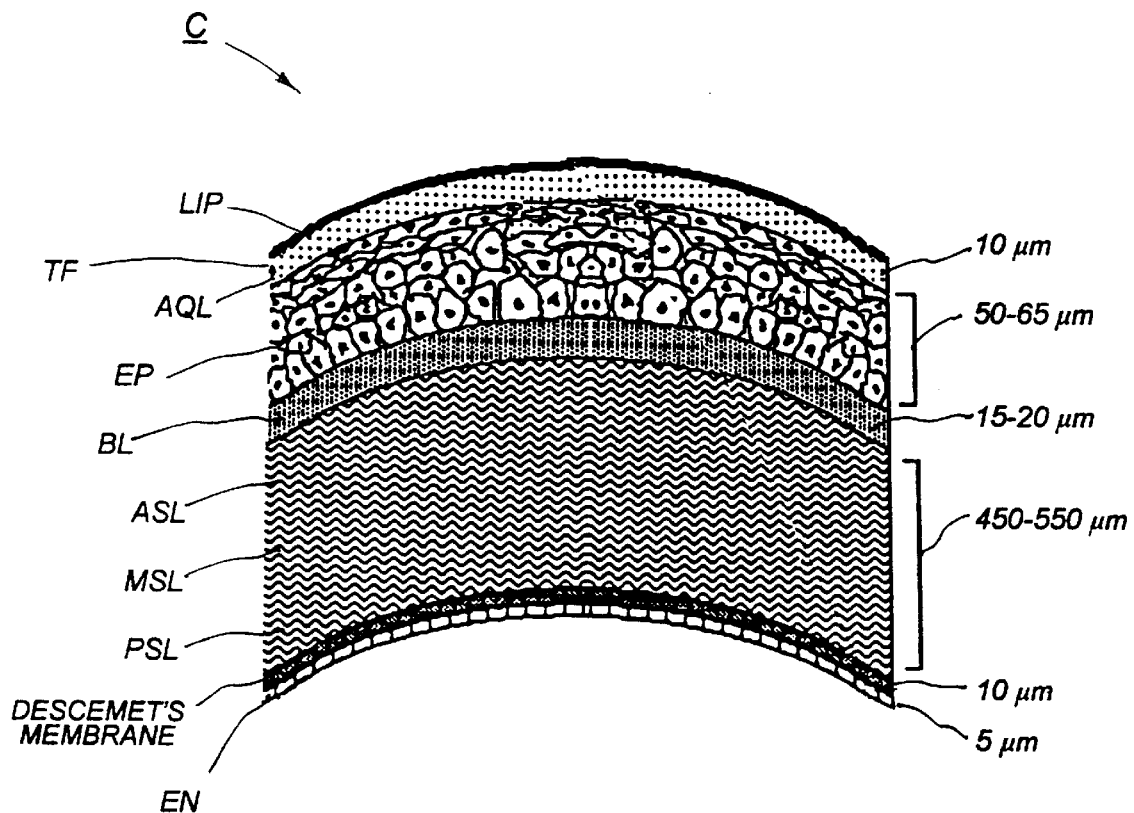
FIG. 2 is a not-to-scale sectional view of a cornea depicting the thicknesses of the various layers in microns.
Figure 3:
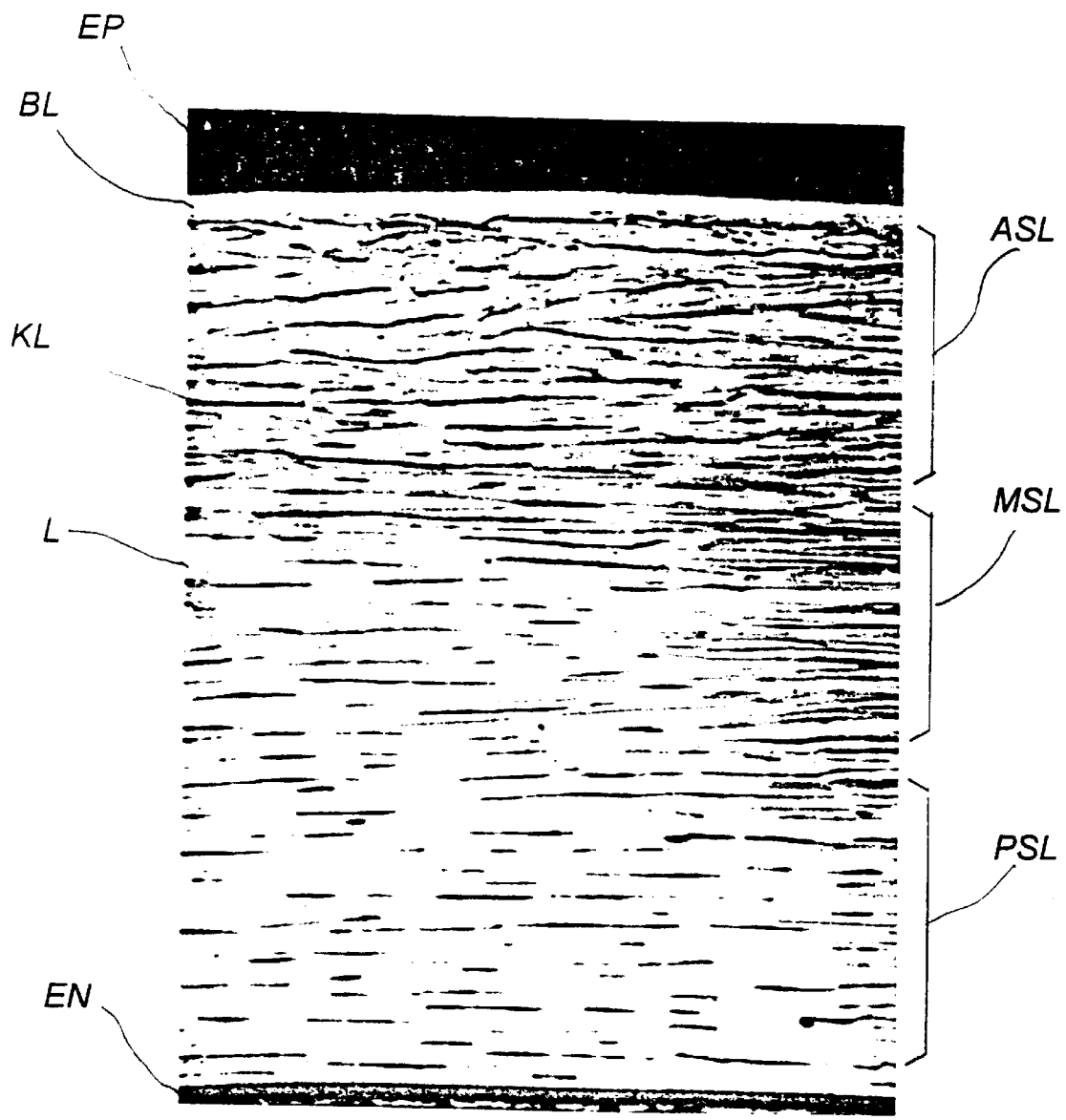
FIG. 3 is a photograph of a cross-section of a cornea showing the interleaving of collagen fibrils between lamellae in the anterior stroma and the lack of such interleaving in the mid- and posterior stroma.
Figure 4A:
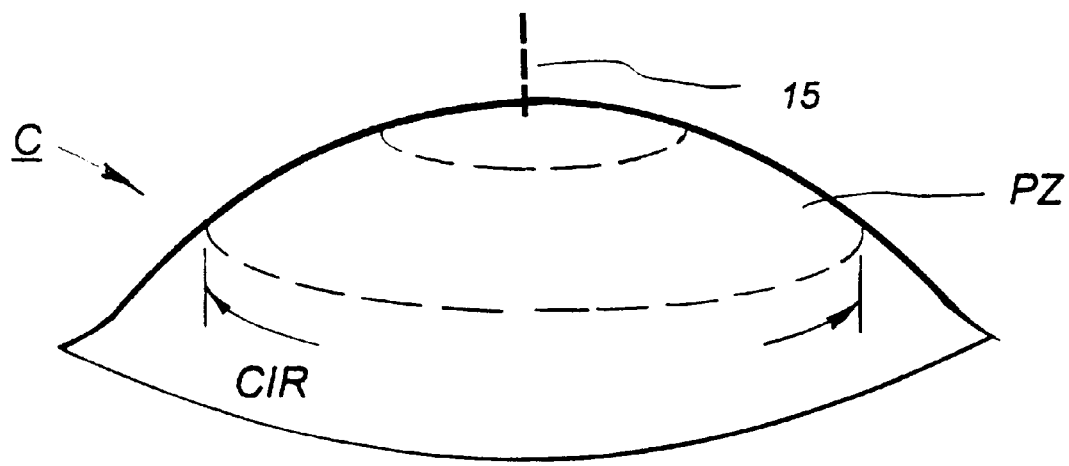
FIG. 4A is view of a cornea indicating the paracentral zone.
Figure 4B:
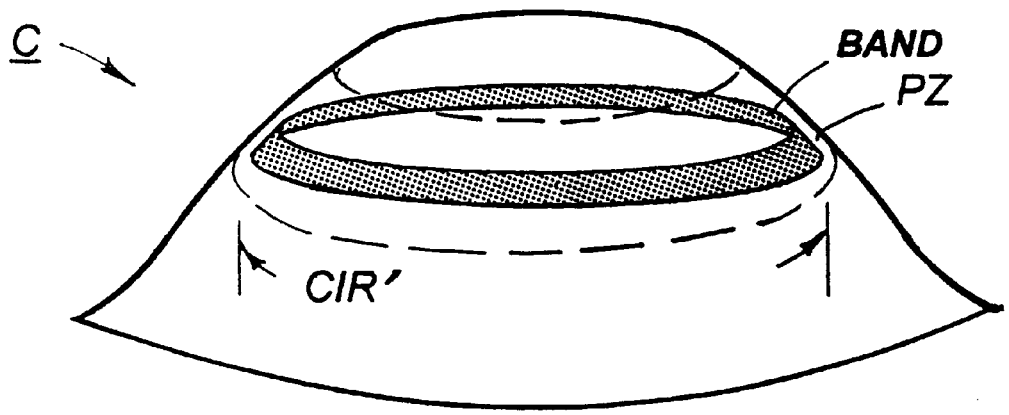
FIG. 4B is view of a cornea showing a circular 360° band of photo-intercalated stromal tissue in the paracentral zone that can maintain a prolate shape in the cornea.
Figure 5:
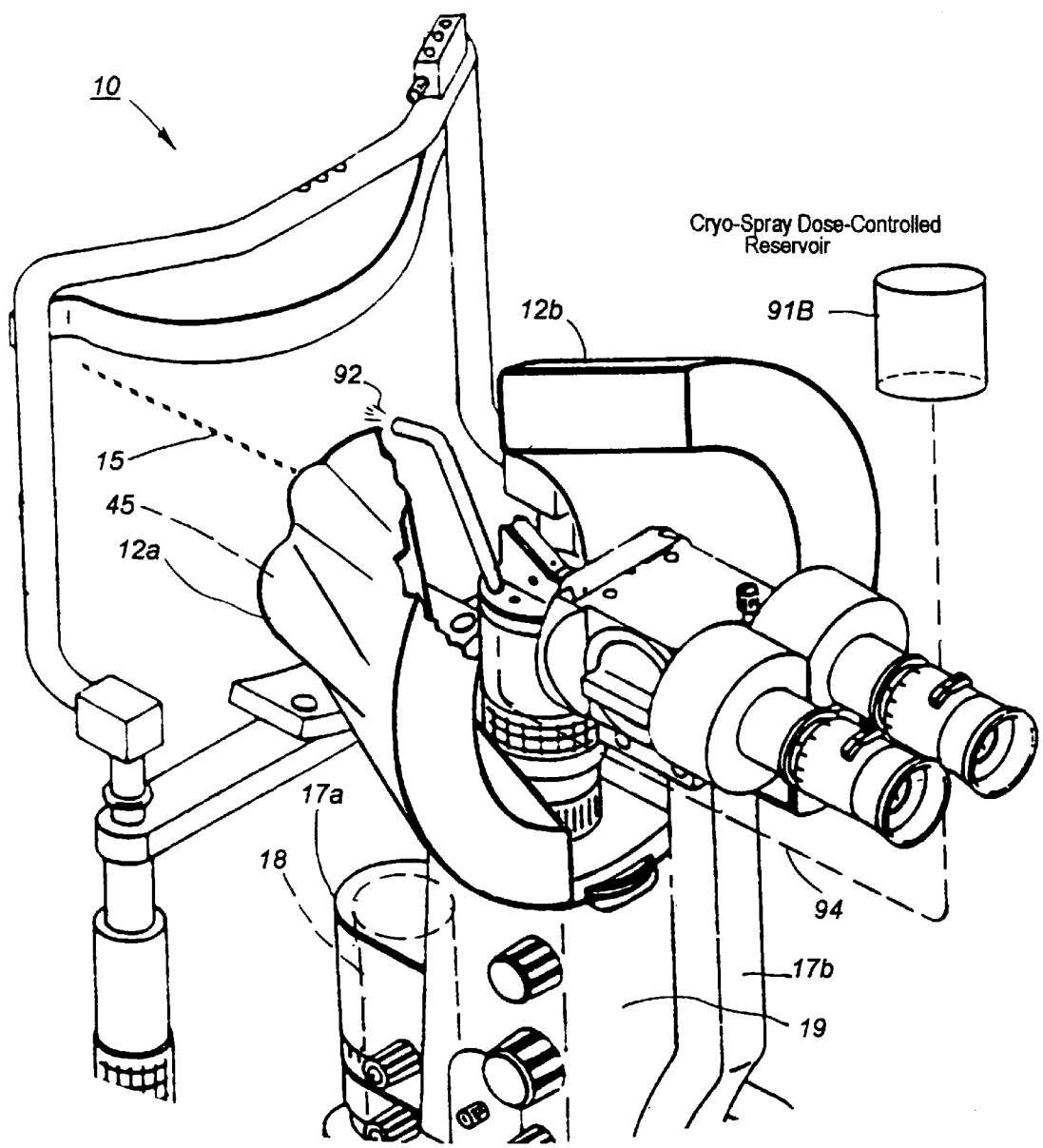
FIG. 5 is an enlarged cut-away view of a portion of the slit-lamp platform of the invention showing a component of the cryo-spray delivery system.

Referring now to FIG. 5, perspective view of the TAOS platform 10 of the present invention are shown. The TAOS system incorporates and carries cooperating energy delivery systems that provide the means to make corneal curvature more prolate (i) by developing an "inverse" thermal gradient in anterior stromal lamellae with a combination of cryo- and photonic energy effects; (ii) by modulating the absorption coefficient and temperature of the anterior cornea prior to photonic irradiation; and (iii) by maintaining and protecting the condition and shape of the anterior corneal surface with a prolate lens-prosthesis thereby allowing "shallow-plane" lamellar photo-microwelding (photo-intercalation of lamellae). The photo-intercalations or melding of the lamellae in a continuous BAND in a shallow-layer at the region of the Bowman's layer BL and anterior stromal lamellae ASL will cause a tightening effect to maintain a prolate-shaped cornea (see FIG. 4B).

In this disclosure, the term TAOS (thermal-adjunct orthokeratology system) is utilized to alternatively describe the apparatus of the invention and the TAOS technique or procedure. When describing the apparatus, the term TAOS platform is used to describe the slit lamp apparatus or platform indicated at 10 in FIG. 5. The TAOS platform 10 carries the cooperating optical systems in left (first) and right (second) housings or frames 12a–12b mounted around optical axis 15 of a slit lamp with biomicroscope 16 that is known in the art. (The reference numeral 15 is used for convenience herein refer to the cornea's optical axis and the platform's optical axis). The platform 10 has $1^{st}$ slit lamp swing-arm 17a and $2^{nd}$ microscope swing-arm 17b that pivot around post 18. The conventional slit lamp module is indicated at 19.

1. Optical Parametric Oscillation Conversion as Photonics Source

Figure 6:
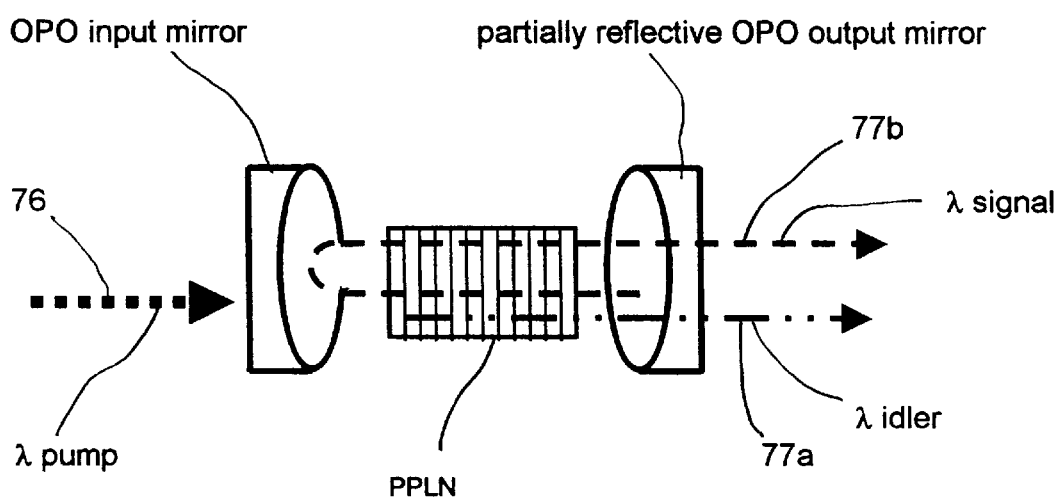
FIG. 6 is a schematic diagram of an optical parametric converter (OPO) or photonic energy source for producing a particular wavelength of photonic energy.

The photonic energy source 75 of the invention may be any laser source, but preferably is an optical parametric oscillator (OPO) system based on the use of nonlinear materials to convert wavelengths from a laser pump source (see FIG. 6). Such an OPO source provides a tunable wavelength system that allows the TAOS system to "tune" the wavelength within the infrared region. Referring to the schematic diagram of FIG. 6, optical parametric oscillation is a non-linear process in which a single "pump" laser beam 76 is transformed into two photonic energy beams 77A and 77b, each with a lower energy, which are called the "signal" beam 77A and the "idler" beam 77b. In other words, this non-linear wavelength conversion process provides a system to convert a single fixed wavelength beam from a laser into two other wavelength beams, wherein the three beams have the following relationship:

$$1/\lambda_{pump} = 1/\lambda_{signal} + 1/\lambda_{idler}$$

Conventional OPO devices are somewhat limited by the availability of non-linear materials that simultaneously satisfy the requirements of phase-matching, optical transmission characteristics and energy conservation. The signal wavelengths 77A in such conventional OPO's are controlled by angle or temperature tuning of crystal refractive indices. Tuning by angle results in restricted angular acceptance of pump beam 76 and walk-off, which restricts OPO interaction length and reduces the efficiency of converting short-pulse pump beams into the signal beam 77A and idler beam 77b. Crystal temperature alteration is useful for wavelength tuning allow it may work only over a small wavelength range. Recently, periodically poled devices have been developed to produce a non-linear OPO conversion technique known as quasi-phasematching (QPM). The process does not rely on inherent crystal material characteristics, such as birefringence, to achieve non-linear wavelength conversion. Underpinning the quasi-phasematching technique is a non-linear material called PPLN (periodically poled lithium niobate ($LiNbO_3$)). PPLN is a QPM material that offers high non-linear coefficients, low optical losses within the wavelength conversion, and engineerable phasematching properties that allow zero walk-off (non-critical phasematching) anywhere in a particular transmission range, e.g., from 0.35 $\mu$m to 5.0 $\mu$m. These PPLN properties have made it accepted as the material of choice for solid-state, high repetition rate, mid-infrared frequency conversion. Lightwave Electonics Corp. of Mountain View, Calif. has developed a multi-watt pulsed PPLN optical parametric oscillator which generates a signal beam at 1.54 $\mu$m, but which may be tuned over a suitable mid-infrared transmission range. It is believed that tuning the OPO from about 1.3 $\mu$m to 1.8 $\mu$m is possible within seconds, with a tuning range from 1.3 $\mu$m to 2.8 $\mu$m being possible within 10's of seconds (see, e.g., Bosenberg W., Drobshof, A., and Myers, L., "High-power, high-repetition-rate, optical parametric oscillator based on periodically poled $LiNbO_3$", reprint 1996 Optical Society of America).

It is believed that the above-described PPLN OPO will be optimal for the TAOS system. It should be appreciated that the term signal beam 77A used herein may include a similar wavelength from any non-tunable photonics source 75, although an OPO the preferred system.

By means of research and analysis of various photonic energy wavelengths in tissue at modulated absorption coefficients and temperatures (described below), the preferred wavelength range for lamellar photo-microwelding lies in a range between about 1.30 $\mu$m and 2.8 $\mu$m. More preferably, the range lies between about 2.56 $\mu$m and 2.70 $\mu$m. Besides using an OPO source described above, a conventional CW or pulsed laser source may used that produces a wavelength in the above range. It should be appreciated that TAOS platform of the invention may be suitable for variants of the TAOS technique disclosed herein (or another distinct modalities such as so-called collagen "shrinkage" at lower target temperature ranges than used in the TAOS technique). For this reason, wavelengths in a wider range from about 1.30 μm to 2.8 μm fall within the scope of the invention for directing photonic energy to create photo-intercalations of anterior stromal lamellae for refractive purposes.

2. Modulation of "Alpha" System: Inverse Thermal Gradient

Of particular interest, the "M-alpha" system 85 provides the means for creating a true "inverse" thermal gradient in tissue for a period of ns to ms during photonic energy delivery, wherein the term "inverse" thermal gradient means that at the instant of irradiation of the cornea, the anterior surface layers will be cooler than subsurface layers—the opposite of a "conventional" thermal gradient wherein surface is elevated in temperature more than subsurface tissue. The novel system is herein called an M-alpha system for "modulation of alpha" ($\alpha$ being usual symbol for absorption coefficient) since the system modulates $\alpha$ as well as temperature of tissue, both effects being caused by the technique of subjecting the cornea to the propagation of a "cryo-wave" therethrough. The absorption coefficient $\alpha$ varies with photonic energy wavelength, tissue hydration and tissue temperature. The M-alpha system 85 not only allows an "inverse" thermal gradient, but also (i) allows for creation of the shallow-plane microweld effects described above in which the photo-intercalations do not extend deeply through tissue, (ii) allows for use of much lower OPO or photonic energy levels to effect the photo-microwelding of lamellar layers than might be expected (i.e., it is believed that lower fluences will be required for such photo-microwelding than for LTK energy delivery to "shrink" large volumes of collagenous tissue, and (iii) allows the use of laser wavelengths not previously used in corneal refractive surgeries. The techniques disclosed herein for delivering such cryo-wave cooling is time-related to photonic energy delivery and both systems are controlled together as described below in the technique of the invention.

Figure 7:
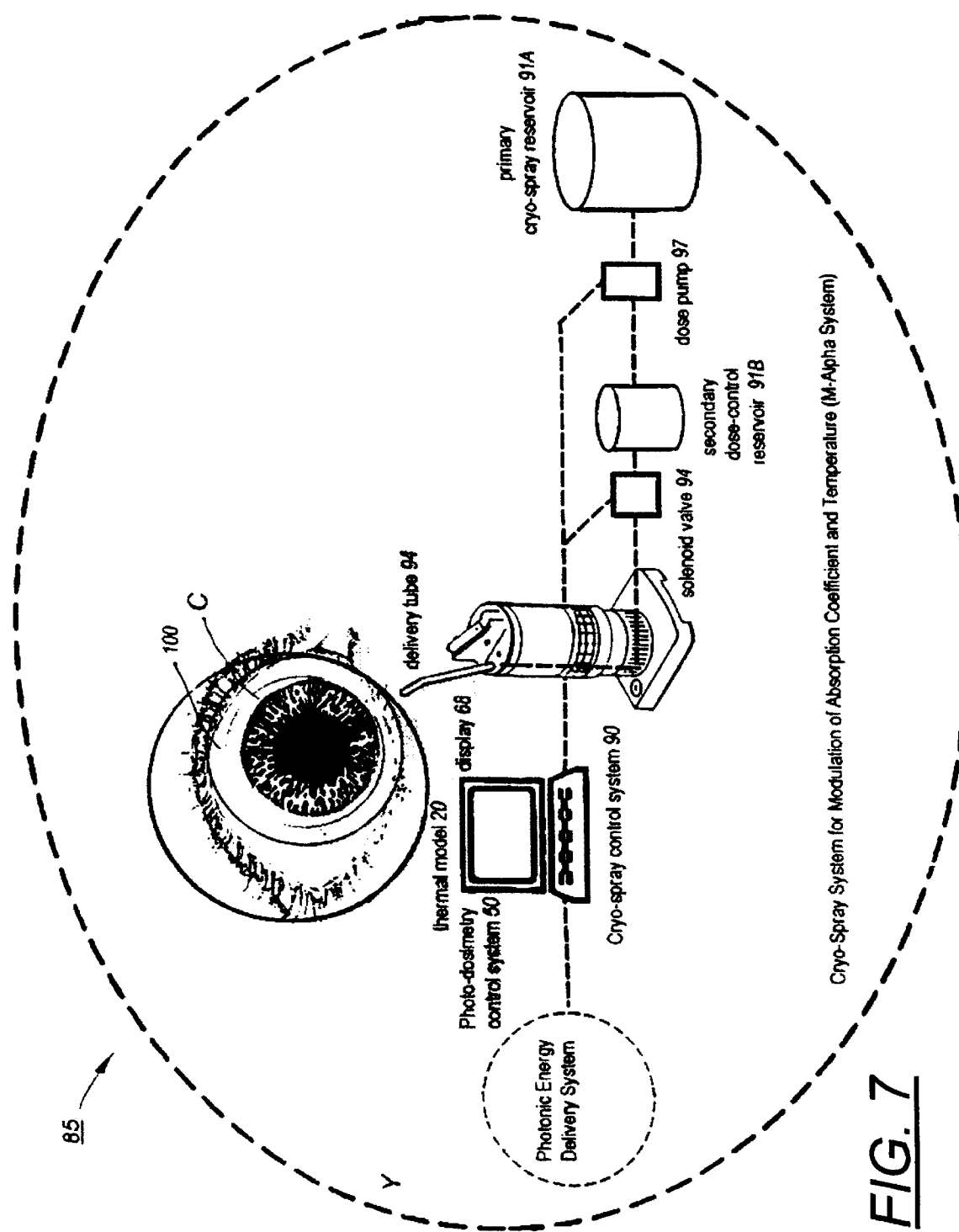
FIG. 7 is a schematic diagram of cryo-spray cooling system of the invention for cooling the cornea prior to photonic energy delivery to create an inverse thermal gradient in the anterior stroma.

Referring to FIG. 7, the M-alpha system 85 has multiple components including a "cryo-spray" or coolant delivery system together with a cyro-dosimetry controller 90. A primary cyro-spray reservoir 91A is provided to carry any suitable coolant or cyro-spray 92, for example a liquid nitrogen, cryogen or other liquified bio-inert gas that has a low boiling point that is comparable to chlorodiflouromethane (which has a boiling point of about $-40°$ C.). The primary cyro-spray reservoir 91A is any suitable insulated canister capable of storing the cryo-spray at the pressures required (5–15 atm). The cryo-spray delivery tube 94 is interrupted by a solenoid valve 96 that is electronically controlled by cryo-dosimetry controller 90 (e.g., a programmable digital delay generator, Model DG 535, Stanford Research, Sunnyvale, Calif.) to emit spurts of cryo-spray with precise timing to about 0.25 ms at the lens-prosthesis over the cornea. Of particular interest, the system includes a secondary dose-controlled reservoir 91B that is intermediate to the delivery tube 94 and the primary cyro-spray reservoir 91A. The secondary dose-controlled reservoir 91B, in use, is adapted to serve as a fail-safe mechanism to allow only a single predetermined dose of cryo-spray to be stored in such secondary reservoir 91B at the time of treatment. Thus, in the timing and duration of delivery, for example, if the solenoid valve 96 were to stick open, only the single cyro-spray dose could be released. Before each use, a manual dose pump 97 other computer-controlled dose pump and valve system loads the secondary dose-controlled reservoir 91B with the pre-determined dose. The cryo-dosimetry controller 90 communicates with photo-dosimetry controller 50 further described below to precisely time the duration of cyro-spray application in relation to photonic energy delivery. Typically, the cryo-spray application ranges from about 1 ms to 500 ms. The cryo-dosimetry controller 90 together with photo-dosimetry controller 50 triggers photonic energy delivery from 0.1 to 500.0 ms following termination of the cryo-spray, which timing is adjustable by the photo- and cryo-dosimetry controllers 50 and 90.

The thermal model 20 (see FIG. 7) of the cornea is adapted to model the application of cyro-effects on the cornea, as well as elevated photo-thermal effects. From such a model, the correct cyro-spray dosimetry can be determined with the objective of identifying (i) the amount of cryo-spray, and (ii) the duration of cryo-spray delivery necessary to alter the temperature of the lens-prosthesis 100 (described below) and the cornea C with the high velocity of propagation of the cyro-wave therethrough. For reasons that will be clear below, the objective of the cyro-spray application is best defined in terms of a "delta" or lowering of temperature in a layer of the cornea, herein referenced by the symbol "$-\Delta t$" (negative change in temperature), which is a function of (i) boiling temperature of cryo-spray; (ii) dose volume of cryo-spray; and (iii) ms time period over which cryo-spray dose is delivered. For example, the objective of cyro-spray delivery may be quantified as "a $-\Delta t$ of about $-15°$ to $-25°$ C."; or "a $-\Delta t$ of about $-25°$ to $-35°$ C.", etc. over a period of n microseconds.

FIG. 7 shows a schematic diagram of the M-alpha system 85. Referring back to FIG. 5, it can be seen that cryo-delivery tube 94 is mounted on the $2^{nd}$ swing-arm 17b or slit-beam module 18 of the TAOS platform or optionally on the pivot post 18. The cryo-delivery tube 94 is of a flexible or adjustable configuration as is known in the art and has a orifice diameter ranging from 0.2 mm. to 2.0 mm. When in use, cryo-delivery tube 94 is positioned from about 5 mm. to 25 mm. from the lens-prosthesis 100 (described below). The lens-prosthesis 100 is adapted to mediate the cryo-wave before it propagates through the cornea as will be described below.

3. Spatial Application (SA) System

The beam spatial application (SA) system 105 or beam pointing component of the invention provides a plurality of photonic beam emitters, preferably between two and four, that can project photonic beams across scanned locations, or at fixed locations, within or about defined paracentral quadrants 107 of paracentral zone PZ of the candidate cornea.

Figure 8:
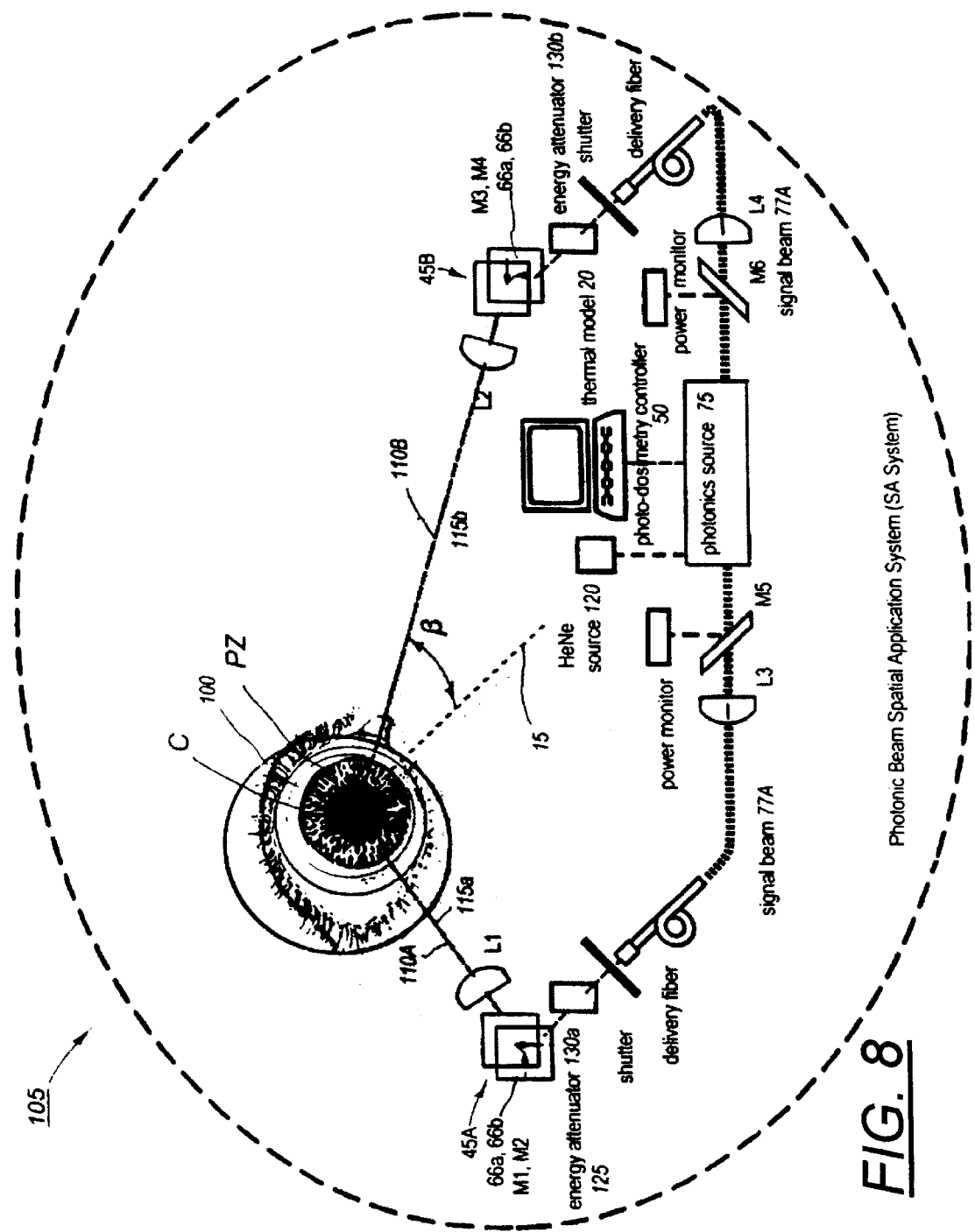
FIG. 8 is a schematic diagram of the photonic beam spatial application system of the invention for directing beams over the anterior surface of the cornea.

FIG. 8 is a schematic diagram of the spatial application (SA) system in which candidate eye 5 and cornea C is in a treatment position at the TAOS platform 10. Cornea C has optical or axis 15, which is herein defined as a central axis of the cornea and lens which directs light onto the retina. A co-axial cylindrical light corridor from about 5 mm. to 20 mm. in diameter is shown around optical axis 15 extending to biomicroscope 16 (see FIG. 5).

FIG. 7 illustrates photonic beam emitter modules 45A–45B, each of which is indicated as emitting a beams 110A–110B that may be projected or steered generally in a scanned pattern within angular scan range about an axis (115a–115b). Each scan range generally covers somewhat greater than 180° of paracentral zone PZ of cornea C. In FIG. 8, the emitter axes 115a–115b represent a "repose" position of each emitter, wherein repose is defined as an axis more or less central to the zone around which the emitter module can scan.

The beams 110A–110B are split components of signal beam 77A and delivered to SA system components via any suitable means such as optical fibers, and the term "emitter module" is used herein to describe the system and point source at which beams 110A–110B are emitted from platform 10 and toward candidate cornea C. As such, the emitter modules 45A and 45B are the final elements in a combination of components, which typically includes, but is not limited to, the OPO conversion source 75 together with fiber optics, lenses (L1, etc.), mirrors (M1, etc.), filters, splitters, combiners, shapers, shutters, power attenuators and including x-y galvanometric scan engines 66a–66b with steering mirrors M or other arrangements operatively connected between photonics source 75 and the emission of the beams 110A–110B. The number (n) of emitters modules are angularly spaced generally in opposition around axis 15 of the platform. The plurality of emitter modules and their opposing symmetrical arrangement relates to an important technique of the invention in treating generally opposing sides of the cornea C thus providing a symmetry and simultaneity of treatment relative to the eye's visual axis 15. This manner of treatment is to be contrasted with an asymmetric or non-simultaneous manner of treatment at one side of the cornea and then the other side (for example with a contact laser probe). Referring to FIG. 8, the emitter modules 45A–45B in this preferred 2-emitter embodiment of platform 10 are spaced at 180° about optical axis 15 such that opposing emitter modules 45A and 45B are generally aligned toward axis 15 within a cross-sectional plane indicated at Y.

Each emitter module 45A–45B includes a computer-controlled independent x-y galvanometric engine (or x-y-z galvos) indicated at 66a–66b along with mirrors M and may be programmed to operate as a raster scanner, vector scanner or step scanner in order to scan in a pre-determined path in paracentral zone PZ. An example of such a galvanometric scanner is a custom-made Single-Axis MO line scan engine with MiniSax Servo Amplifier, including parts 310-186071, 000-3004006 and 000-3004566, from General Scanning, Inc., Watertown, Mass. 02127.

Now turning to FIGS. 15A and 15C, it can be seen that emitter modules 45A–45B are carried in first and second housings 12a–12b fixed to vertical support 18 of platform 10 although any suitable housing or frame may carry the emitter modules. Repose axes 115a–115b along which each emitter 45A–45B emits the beams 110A–110B are angled relative to axis 15 at angle β which may range from about 15° to 60°; and preferably is from about 30° to 50°. In other words, referring to FIG. 25, each emitter axis 115a–115b in its repose position is preferably angled close to perpendicular to the anterior surface of the cornea. The distance of the emitter from the cornea is from about 20 mm. to 200 mm. outward from the anterior corneal surface.

Also shown in FIG. 8 of SA system 105 is a visible aiming beam as is known in the art, e.g., a HeNe laser source indicted at 120 operating at 632.8 nm or any other suitable visible laser. It can be seen that housings 12a–12b and other components are carried on movable base 122 with joystick 124 as is known in the art for moving the slit lamp systems relative to the patient's cornea C.

4. Prosthetic Corneal Contact Lens

Figure 9:
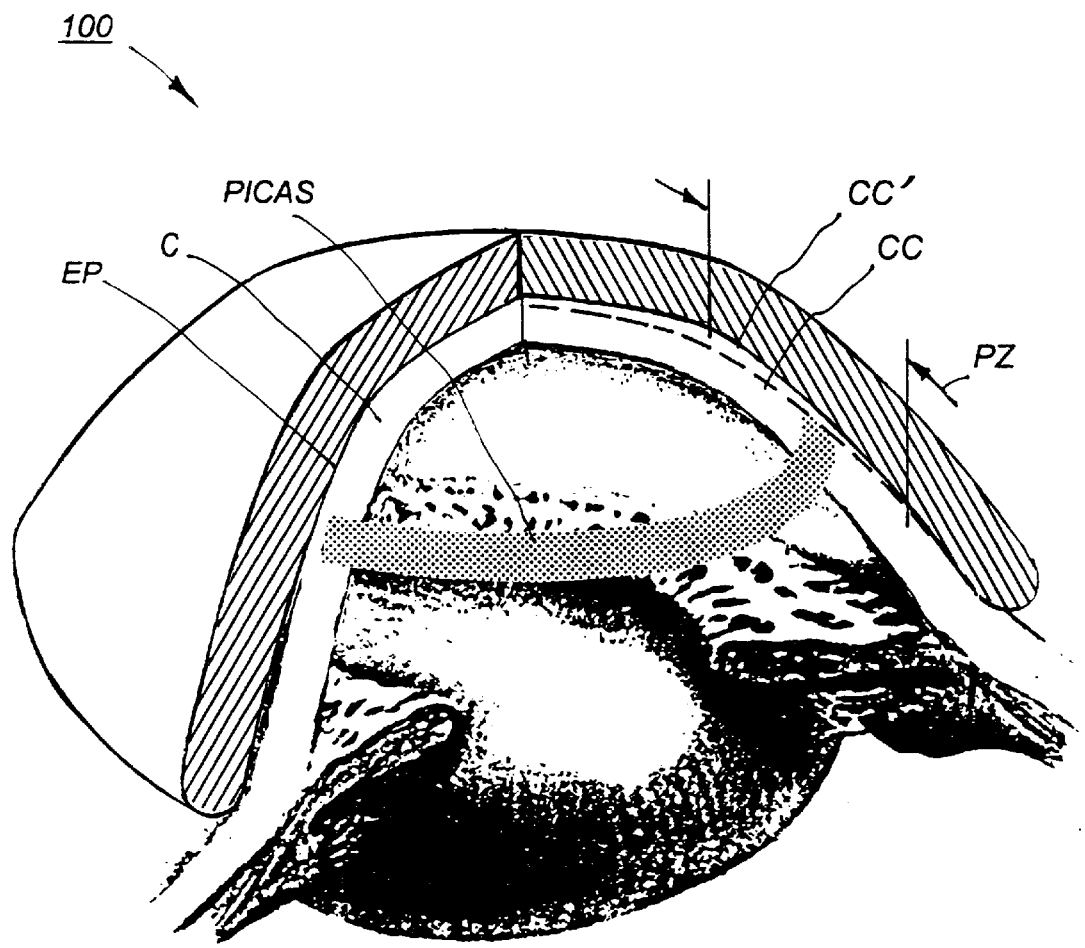
FIG. 9 is a cut-away view of a prosthetic lens of the invention showing its prolate base curvature and fitted over a cornea.

The TAOS technique of the invention preferably is performed with a corneal prosthesic lens 100 in place which serves multiple therapeutic purposes. Referring to FIG. 9, the lens-prosthesis 100 serves three important roles: (i) shape-maintaining the anterior cornea surface in a desired form (both locally flat and globally curved in a particular prolate shape) while the lamellar photo-intercalation technique is performed, (ii) protecting the epithelium from damage both from the cryo-effects of the cooling wave and from thermal shocks associated with photonic energy delivery, both of which effects propagate through the epithelium EP and stroma S, and, (iii) maintaining an intact tear film TF during the treatment to allow consistent photo-thermal modeling.

In the "shape-maintaining" role, the lens-prosthesis 100 is similar to that of a orthokeratology treatment, i.e., maintaining a corrected or preferably slightly over-corrected corneal curvature for the period of treatment. In the case of conventional orthokeratology, the treatment period is a matter of days. In the case of thermal-adjunct orthokeratology or TAOS, the treatment period is a matter of fractions of a second, or a number of seconds in the case of repetitive energy deliveries. As will be described below in Section 10 concerning the TAOS technique, the role played by lens-prosthesis 100 is unique in that the epithelium EP is maintained between ambient environment temperature (about 25° C.) and a physiologic temperature (about 36°–39° C.) during the treatment, except for a period of time ranging from about 0.1 ms to 500 ms. More important, the fractional period of time in which the epithelium EP and anterior lamellae ASL are outside the ambient-to-physiologic temperature range, the temperature still will be above about 5° C. to 15 C., and therefore such cooling should not cause significant epithelial cell death from any cryo-effects.

The technique of the invention requires a prosthetic lens 100 with fill corneal coverage. To this end, the prosthesis preferably is from about 12.0 to 16.0 mm. in diameter or larger as it may be adapted to extend over the sclera (not shown in FIG. 9). The prosthesis is a rigid parallel-sided shell of uniform thickness that is afocal and may be selected with the appropriate prolate shape or base curvature (FIG. 9). The material of the lens-prosthesis is any suitable material known in the art (i) that is transparent to photonic energy transmission without significant absorption (e.g., sapphire, quartz, polymethylmethacrylate, other plastic) with an optimal index of refraction, and (ii) that is an excellent conductor of cryo- or thermal effects. The thickness of prosthesis 100 may be any suitable dimension. Also, gas-permeable lens-prostheses fall within the scope of the invention.

5. TAOS Technique and Dosimetry Control Systems

Whereas the preceding sections have described the collective means necessary for (i) producing the photonic energy beams of appropriate wavelengths, and (ii) controlling the spatial application of such radiative beams over the anterior corneal surface, this section describes the integration of the separate techniques required for the beam's photonic energy to be absorbed within precise shallow layers within the cornea C to accomplish the "shallow layer" photo-microwelding or photo-intercalation of anterior stroma for presbyopic corrections.

Assume the patient's cornea has been prepared for the TAOS treatment with a local anesthetic and is positioned at the slit lamp platform 10. Thereafter, the lens-prosthesis 100 is placed over the cornea as shown in FIG. 9.

Figure 10:
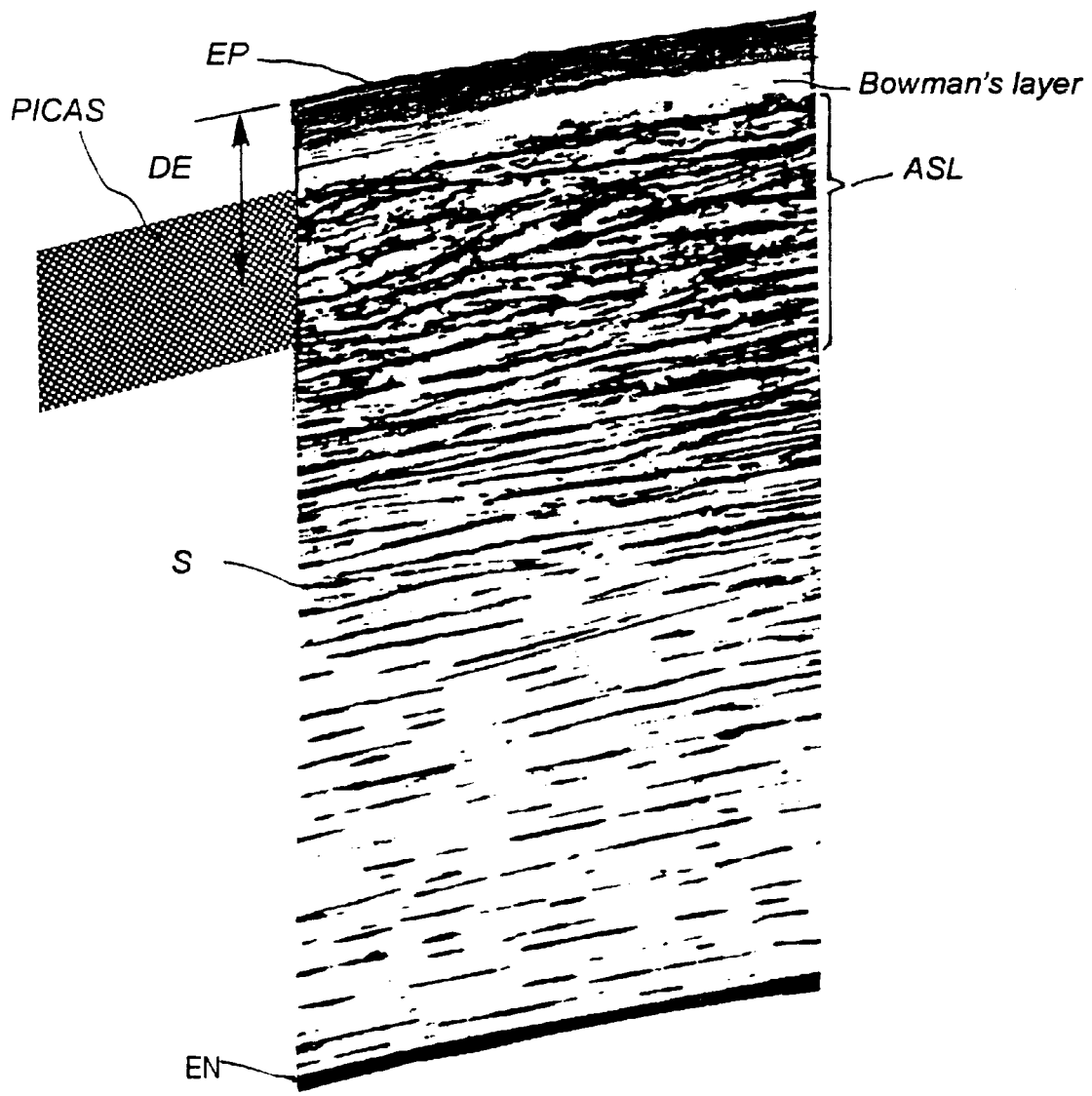
FIG. 10 is a photograph of a corneal section showing a "depth" treatment map that is prepared to perform the technique of the invention.

Referring now to FIG. 10, the sectional view of the cornea shows the region that is targeted for the photo-intercalation at depth DE which is preferably within the anterior stroma lamellae ASL, or in the Bowman's layer BL+ASL as described previously.

Referring back to FIG. 9, a cut-away view of the candidate presbyopic cornea is shown with the pre-treatment anterior corneal curvature indicated at CC. FIG. 9 further shows prosthetic lens 100 in place with the anterior surface being more prolate (steepened in paracentral region) to provide corneal curvature CC', which is either the desired prolate curvature or a slightly over-corrected curvature compared to the desired post-treatment corneal curvature.

Now turning to FIGS. 11A–11F, a millisecond-by-millisecond sequence illustrates the technique of modulating the temperature and absorption coefficient α with the M-alpha system 85. The propagation of the "cryo-wave" with wavefront 155 through the tissue medium takes only between nanoseconds (ns) and milliseconds (ms). Further investigations are being conducted to determine the exact velocities of wave propagation. For this reason, the unit of time shown in FIGS. 11A–11E is an "arbitrary unit" abbreviated as a.u. wherein 1 a.u.=1 ns to 100 ms.

Figure 11C:
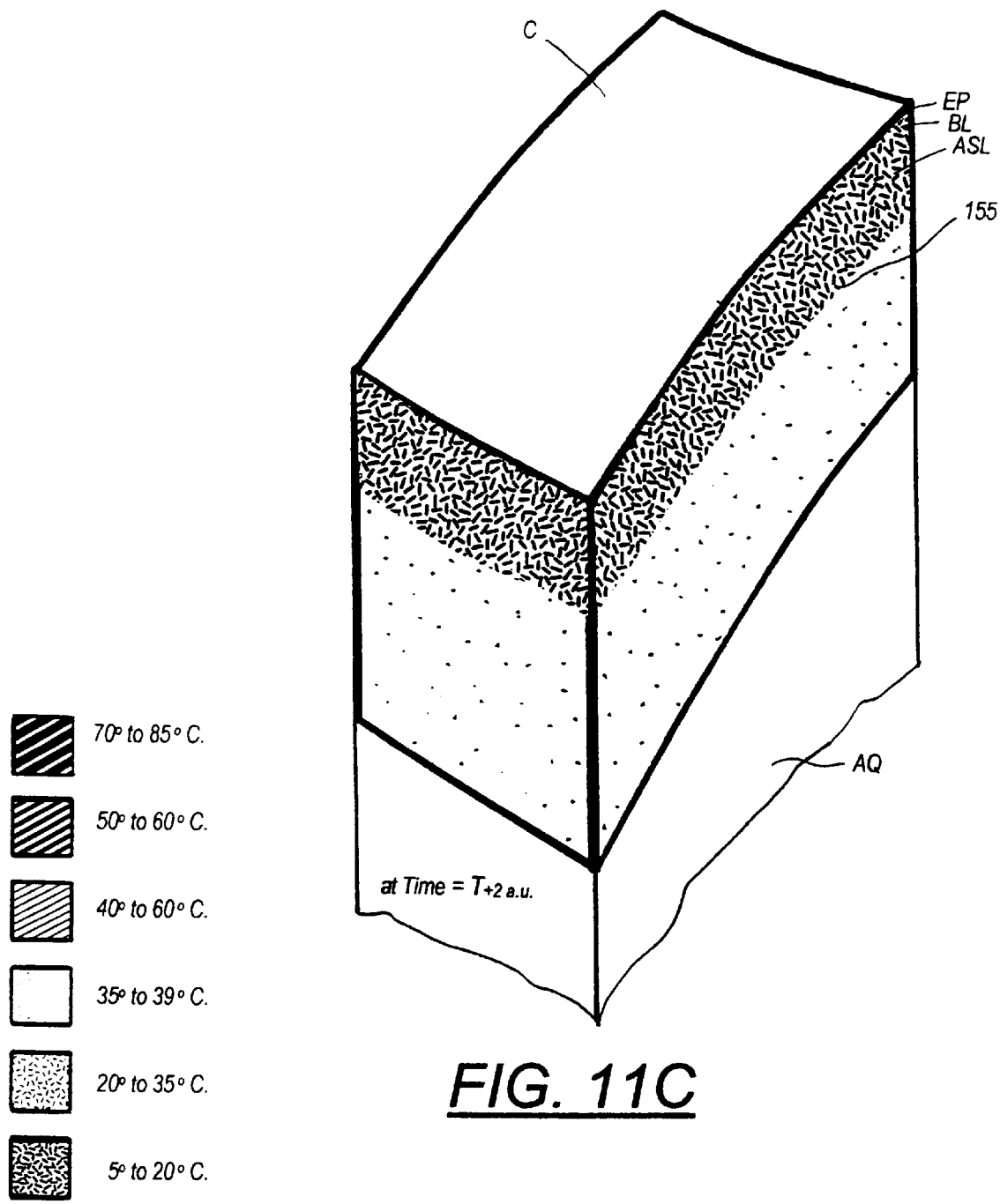

FIG. 11A is an illustration of a volume of corneal tissue similar to the photograph of FIG. 10 under pre-treatment conditions at physiologic temperature at time $T_{zero}$. The lens-prosthesis 100 is shown in phantom view. Boxes to the left of FIGS. 11A–11E indicate graphic patterns that indicate temperatures relating to various "deltas" (changes) in temperature above and below physiologic temperature. For convenience, the temperature ranges are increments of about 10° to 15° C. The temperature ranges shown are particular ranges which are instructive for this disclosure, from <5° C. to >85° C. on either side of physiologic tissue temperature. Physiologic temperature is indicated at between 36° to 39° C.

FIG. 11B illustrates the instant at time $T_{+1\ a.u.}$ when the cryo-dosimetry controller 50 first triggers the cryo-spray system 85 resulting in a spurt of cryo-fluid spray 92 contacting lens-prosthesis 100 (phantom view) at which time it instantly begins to boil off the prosthesis surface. Within nanoseconds, the cryo-effect results in a −Δt of about 25° to 30° C., i.e., the prosthesis is lowered to the 5° to 15° C. range. Instantly, the cryo-wavefront 155 begins to propagate through the cornea in FIG. 11B with the epithelium EP and anteriormost stroma ASL of the cornea also having a −Δt of about 25° to 30° C. and reaching the 5° to 15° C. range.

FIG. 11C depicts time $T_{+2\ a.u.}$ at which time the cryo-fluid 92 continues to boil off the anterior surface of the prosthesis (not shown). Within a period of between about 10 nanoseconds and 10 milliseconds, FIG. 11C shows the cryo-wave and wavefront 155 propagating still further through the cornea C such that anterior stroma ASL has a −Δt of about 25° to 30° C., or in other words such layers are lowered to the range of 5° to 15° C.

Figure 11D:
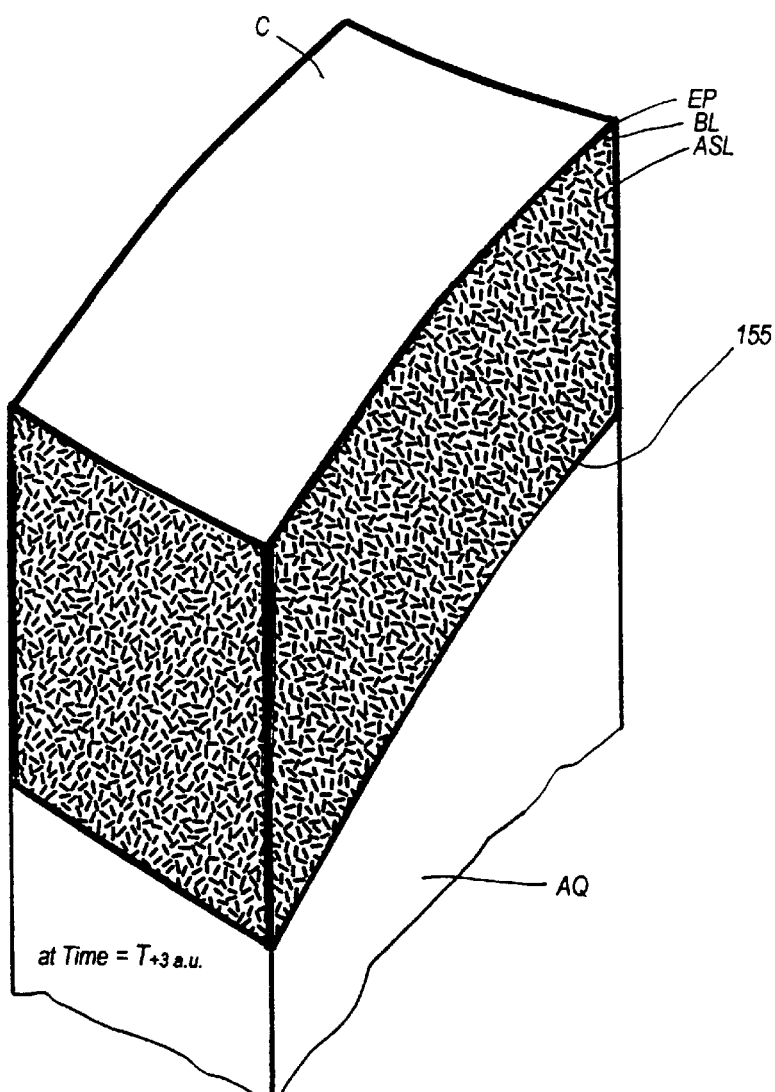

FIG. 11D depicts time $T_{+3\ a.u.}$ wherein the cryo-fluid spray is terminated by cryo-dosimetry controller 90. Within a period of 100 ns to 10 ms, FIG. 11D shows the cryo-wavefront 155 propagating all the way through the cornea C until the cryo-wave strikes the cornea-aqueous AQ interface. The thermal mass of the aqueous AQ absorbs the cooling wave.

Figure 11E:
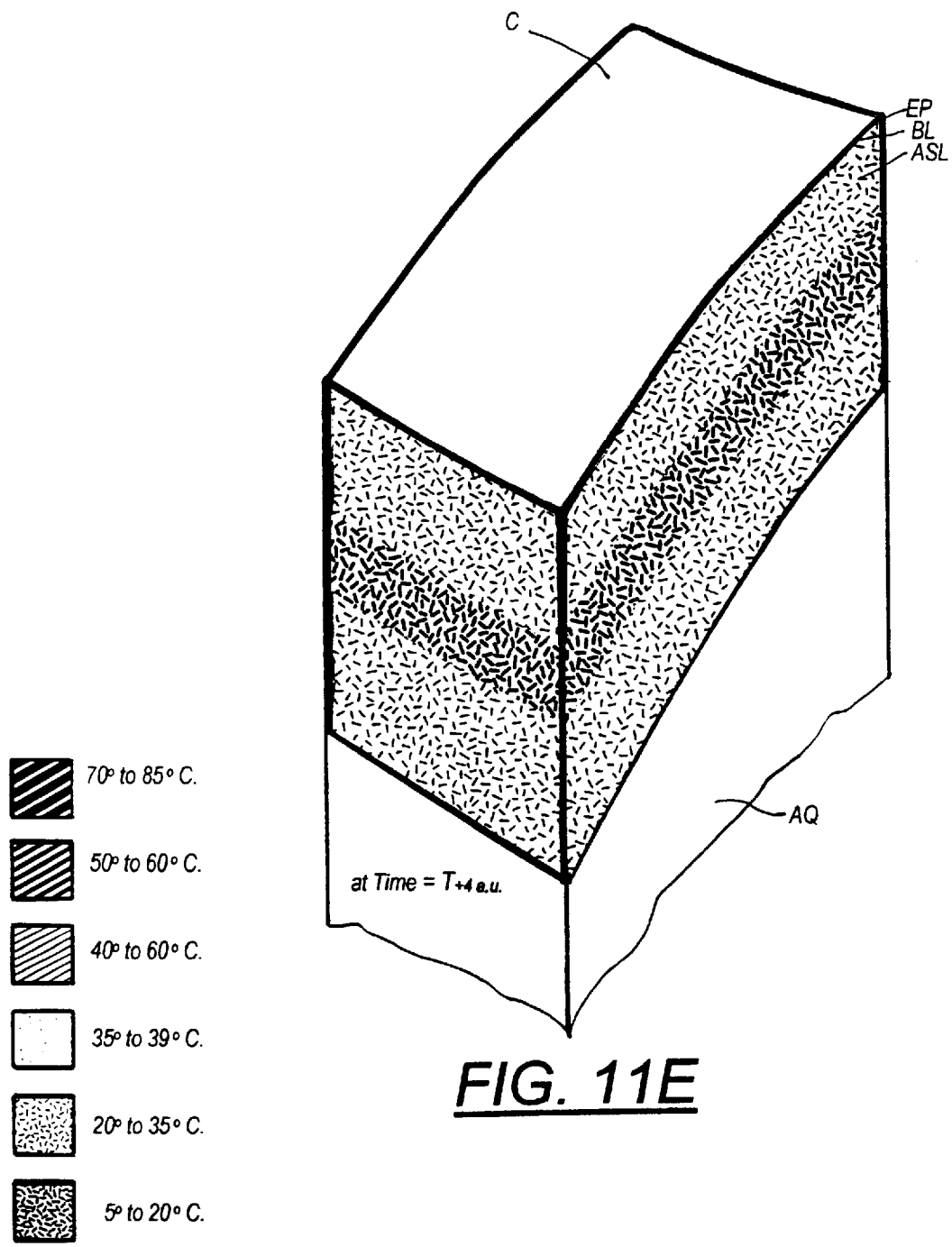

FIG. 11E depicts time $T_{+4\ a.u.}$ with indicating that the cryo-wavefront 155 has stopped propagating and the cornea C is beginning to move back toward physiologic temperature with the cryo-effects being conducted away both to the aqueous AQ and to the warming prosthesis 100 (not shown).

Figure 11F:
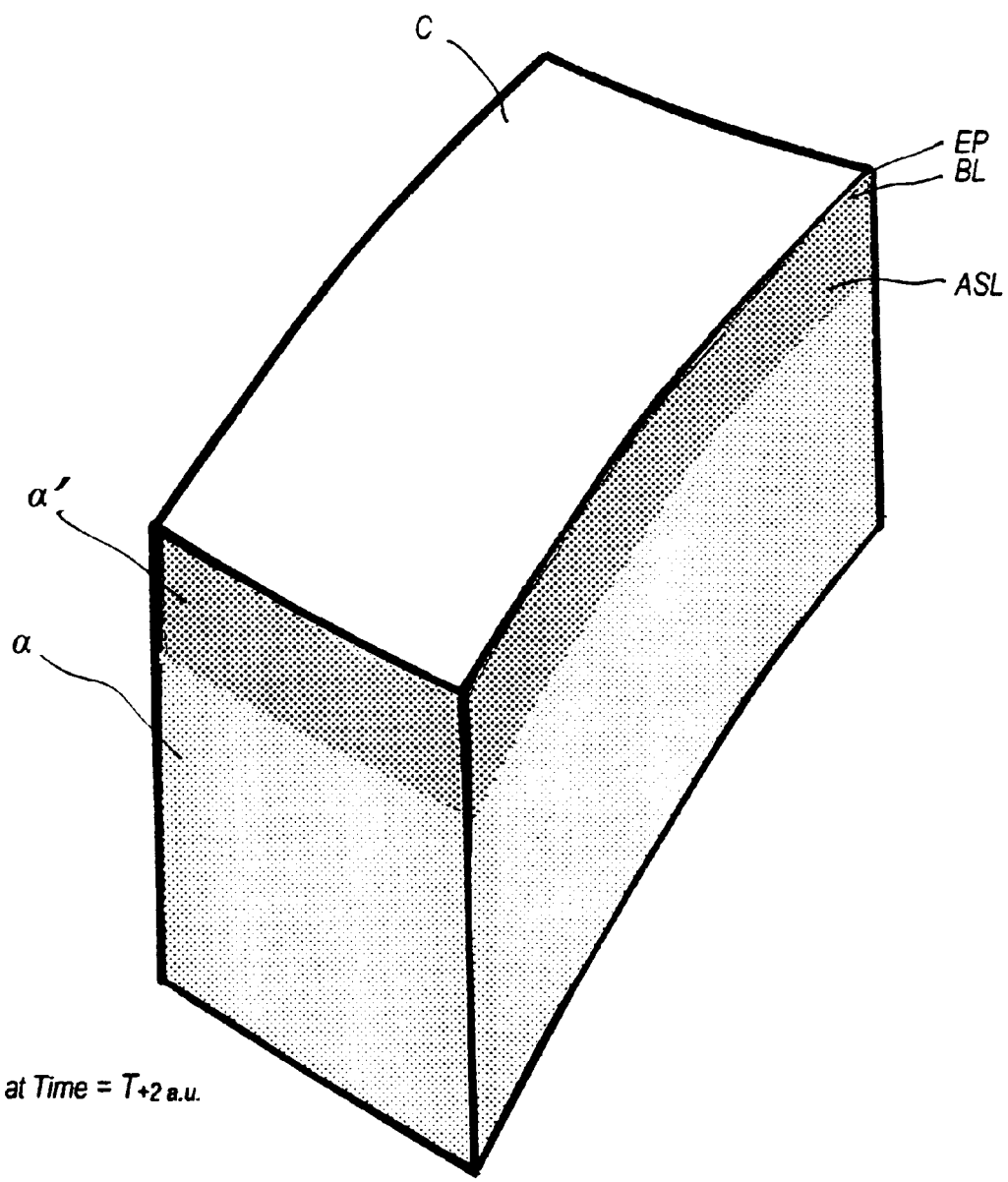
FIG. 11F is a view taken at the instant in time of FIG. 11C but showing a gradient created in the absorption coefficient (α) of the tissue layers.

Now turning to FIG. 11F, it can be illustrated how the M-alpha system 85 modulates the absorption coefficient α of corneal layers. FIG. 11F depicts the cornea's α at time $T_{+2\ a.u.}$ which corresponds to time in FIG. 11C which shows the temperature gradient. At time $T_{+2\ a.u.}$ the leading edge or wavefront 155 of the cryo-wave is in the anterior stroma ASL and absorption coefficient is modulated to α' as indicated by shading, whereas the more mid- and posterior stroma of the cornea has not yet been hit by the cryo-wave, which are still at physiologic absorption coefficient α.

Of particular interest, it can now be seen that at time $T_{+2\ a.u.}$, a desired condition has been created in the anterior stroma ASL wherein there exists a boundary on either side of which the lamellar region has a different absorption coefficient, i.e., α and α' on either side of a propagating cryo-wavefront 155. In other words, this boundary or differential absorption coefficient front moves at the velocity of wavefront 155, and can be utilized to create the "inverse" thermal gradient as described next to develop a subsurface photo-microweld. The cyro-wave's propagation through the tissue may be indicated as having a velocity $V_{CW}$ (velocity of cyro-wave) and can be measured in μm/ns (microns per millisecond). It is believed that $V_{CW}$ is of a magnitude such the approx. 500 μm thickness of the cornea C is traversed by the cyro-wave or shock-wave in the range of 10 ns. and 10 ms. The exact velocity $V_{CW}$ of cryo-wave propagation in the cornea is being investigated. However, the precise $V_{CW}$ range is less important than its relative velocity. It is known that the velocity of photon beam propagation ($V_P$) is much faster. That is, $V_P$ is essentially the velocity of light in media with a given refractive index.

Figure 12C:
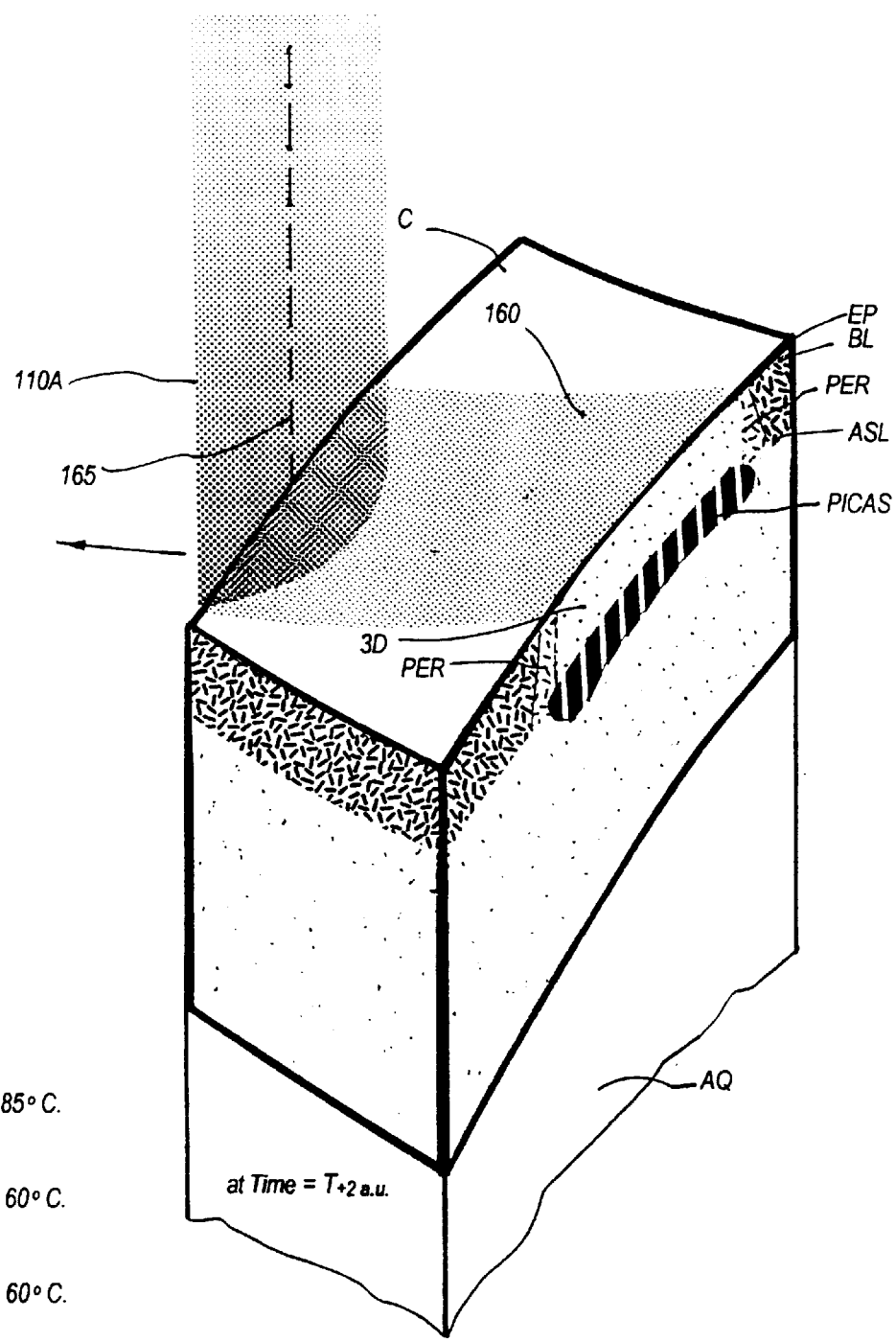

FIGS. 12A–12E now illustrate the true "inverse thermal gradient" that is created by the invention by "mixing" the incidence of (i) cyro-wave propagation with (ii) photonics propagation. FIGS. 12A and 12B are similar to FIGS. 11A and 11B, indicating that at time $T_{+1\ a.u.}$, the cryo-spray system 85 begins to cool the cornea. FIG. 12C is the important Figure to note as it depicts the sequence of timing the photo-dosimetry controller 50 at time $T_{+2\ a.u.}$ to direct beam 110A along surface path 160 through the prosthesis 100 (not shown) to strike the cornea C. Since $V_P$ (the velocity of photon beam propagation) is much faster than the range of $V_{CW}$, the photon beam 110A overtakes the cryo-wavefront 155 at time $T_{+2\ a.u.}$ which results in the photon-tissue interaction depicted in FIG. 12C. As described above, when the photonic beam 110A is absorbed in tissue medium, by chromophores or scattering, the energy in beam 110A is imparted to the absorbing medium along the axis 165 of beam propagation. The photonic energy that is absorbed by the medium and heats the absorbing volume instantly, for example in a period ranging from femto-seconds to pico-seconds. All of the energy in the photonic beam 110A is deposited in the tissue within an extinction length (a quantifiable unit that is absorption coefficient-dependent) of beam 110A. The three-dimensional volume 3D of the lamellar medium that is elevated in temperature can be seen by the perimeter PER of the photon-tissue interaction, which is dependent on (i) beam diameter, and (ii) extinction length of the selected wavelength (with little adjustment needed for scattering) and, (iii) beam scanning speed. The critical fact is that the "delta" or increase in temperature (+Δt) caused by photon absorption relates to the tissue's pre-photon absorption temperature. In other words, at time $T_{+1\ a.u.}$, the most anterior layers of cornea C in FIG. 12B are at temperature range 5° to 15° C. The photo-dosimetry controller 50 directs the photonic source 75 to produce the pulse duration and scanning speed that results in a fluence (about 50 mJ/cm³ to 300 mJ/cm³) which is projected by model 20 to cause a +Δt of about 35° to 40° C. above its pre-irradiance temperature. As described above, the thermal model 20 can generate fluence levels in tissue that predict any desired +Δt, (e.g., "a +Δt of about 25° to 30° C."; or "a +Δt of about 35° to 40° C." etc.).

Thus, In FIG. 12C, the photon absorption at time $T_{+2\ a.u.}$ causes a +Δt in that three-dimensional volume 3D of 35° C. or to the range indicated by shading at 35° to 45° C., or more preferably 36° to 39° C., or physiologic temperature which is in the center of that range. Thus, the epithelium EP above the anterior stroma lamellae ASL in which the beam 110A propagates along path 165 is returned to approximately physiologic temperature. It is believed that the cryo-wavefront 155 shifts the affected volume's α by a significant amount, for example 25 to 33 percent, which is of course dependent on the slope of the wavelength/absorption coefficient curve. The objective of this technique is thus to maintain the epithelium and anteriormost corneal layers at significantly less than 42° to 46° C., which is the range in which cell death occurs, and the fluence and +Δt is selected with this objective in mind.

Still referring to FIG. 12C, it also can be seen that at time $T_{+3\ a.u.}$, the photon beam's $V_P$ (velocity of photon propagation) overtakes the cryo-wavefront 155 and deposits its energy just in front of the advancing wavefront. Thus, at time $T_{+2\ a.u.}$, the stromal region just in front of the cryo-wavefront 155 can be photo-microwelding or photo-intercalated, hereafter indicated as PICAS for photo-intercalated anterior stroma. As can be seen is FIG. 12C, the absorption of photons in the targeted region causes the particular desired fluence in mJ/cm$^3$ that yields the +Δt of about 35° to 40° C., or 40° to 45° C. Since the physiologic tissue temperature was about 36° to 39° C., the photon absorption elevates the irradiated volume's temperature to about 70° to 85° C. In the upper end of that range, it is believed from about 75° to 85° C., is the optimal range for photo-microwelding which is thus achievable. This technique creates a true "inverse" thermal gradient in corneal tissue for at least several ns (nanoseconds) or ms (microseconds) at or about time $T_{+2\ a.u.}$ which is believed to be sufficient time to create the desired PICAS region or photo-microwelded BAND. In other words, the inverse thermal gradient exists at approximately time $T_{+2\ a.u.}$ wherein the epithelium EP and most anterior corneal layers are at physiologic temperature while the targeted region is at a temperature level of 75° to 80° C. or more that will denature collagen molecules, other proteins and cells, resulting in a melding or intercalation of such lamellar tissues as described above. In other words, a welded BAND is created about the paracentral zone PZ to maintain the cornea in the desired prolate shape.

Figure 12D:
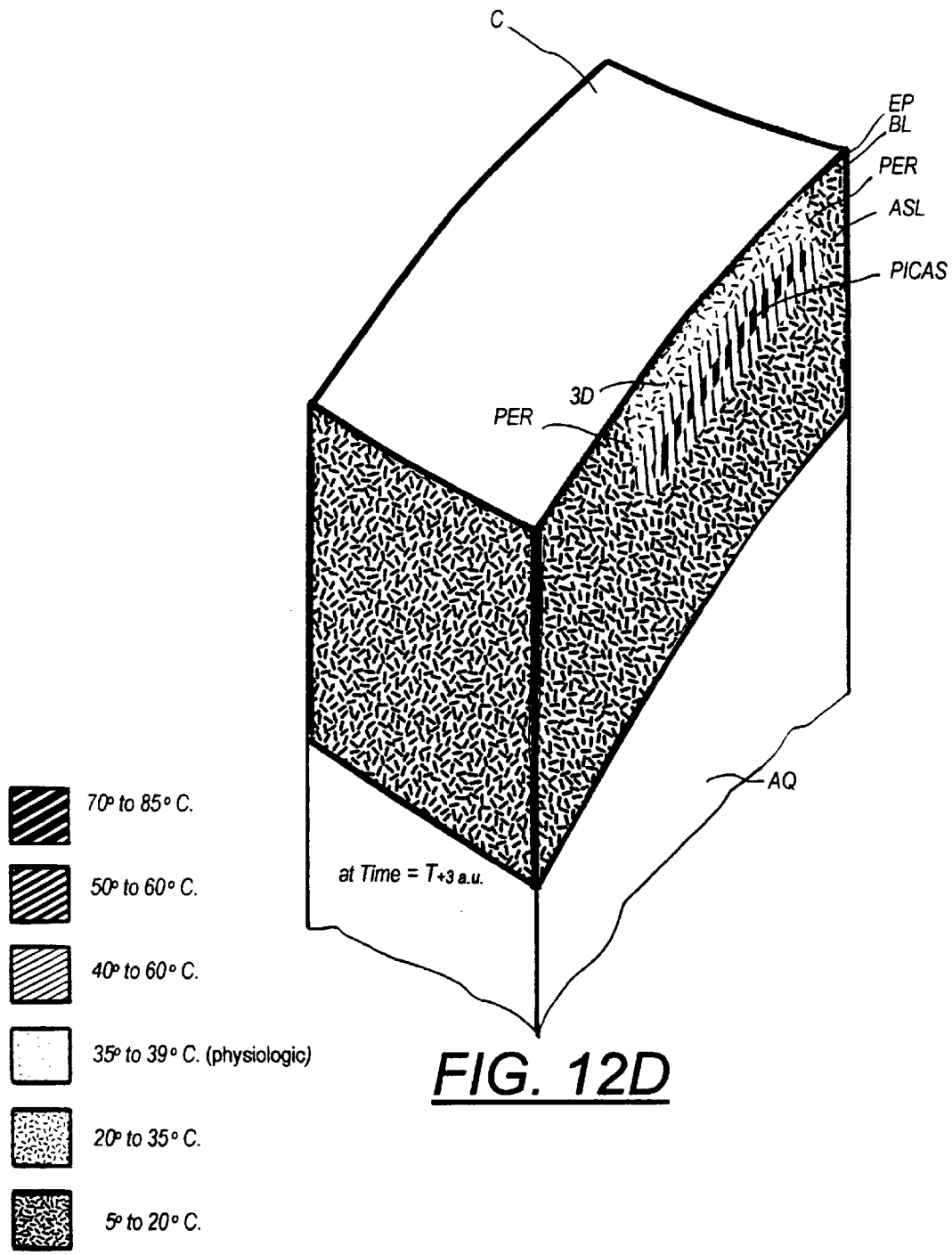

Of particular interest to the technique, FIG. 12D depicts the targeted three-dimensional volume 3D at time $T_{+3\ a.u.}$ (FIG. 12C) wherein the nanoseconds or microseconds of beam irradiance has terminated and the cyro-wavefront 155 overtakes the targeted region 3D. The −Δt of about −30° to −35° C. associated with the advancing cryo-wavefront thus reduces the now photo-microwelded lamellar layers to a lower temperature, for example to the range of 40° to 50° C. range. No matter the exact level of temperature reduction, such a −Δt serves the important purpose of limiting the diffusion of heat outwardly from the now photo-intercalated region PICAS thus providing a distinct margin to the melded-together region.

Figure 12E:
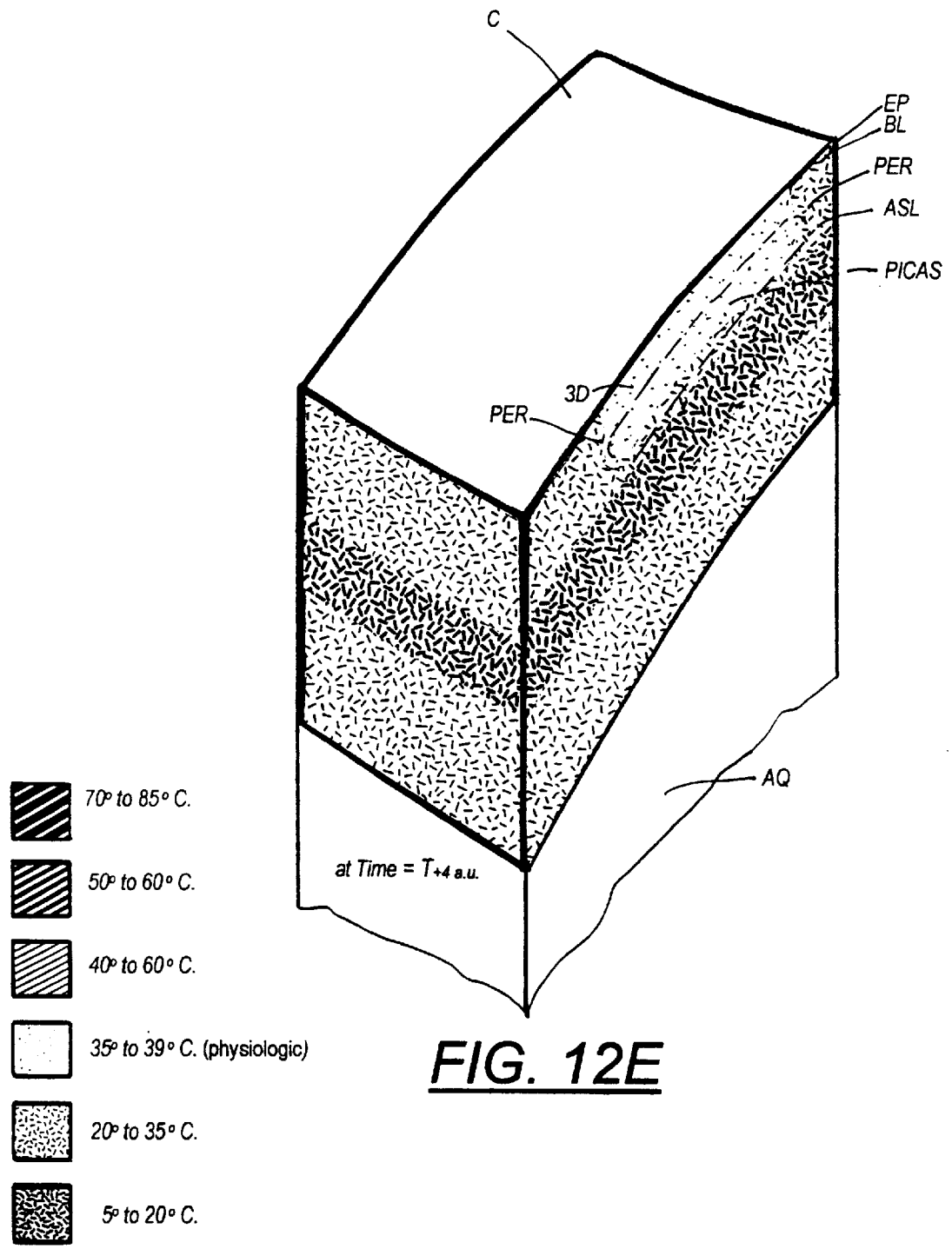

FIG. 12E depicts the corneal volume and isotherms at time $T_{+4\ a.u.}$ wherein the cyro-wavefront 155 has traversed the cornea and the cornea is moving back toward its physiologic temperature. It should be appreciated the FIGS. 12A–12E show only a small section of the photo-microwelded region and the SA system of the TAOS platform is also scanning the photon beam over the pre-designated zone 74 of the cornea. It is believed that the cornea will be maintained approximately in modified curvature CC' (see FIG. 9) by the intercalated region PICAS if the lens-prosthesis 100 were removed, which is an optional aspect of the TAOS technique. More preferably, the lens-prosthesis 100 is left in place for a period of 12–72 hours.

Figure 12F:
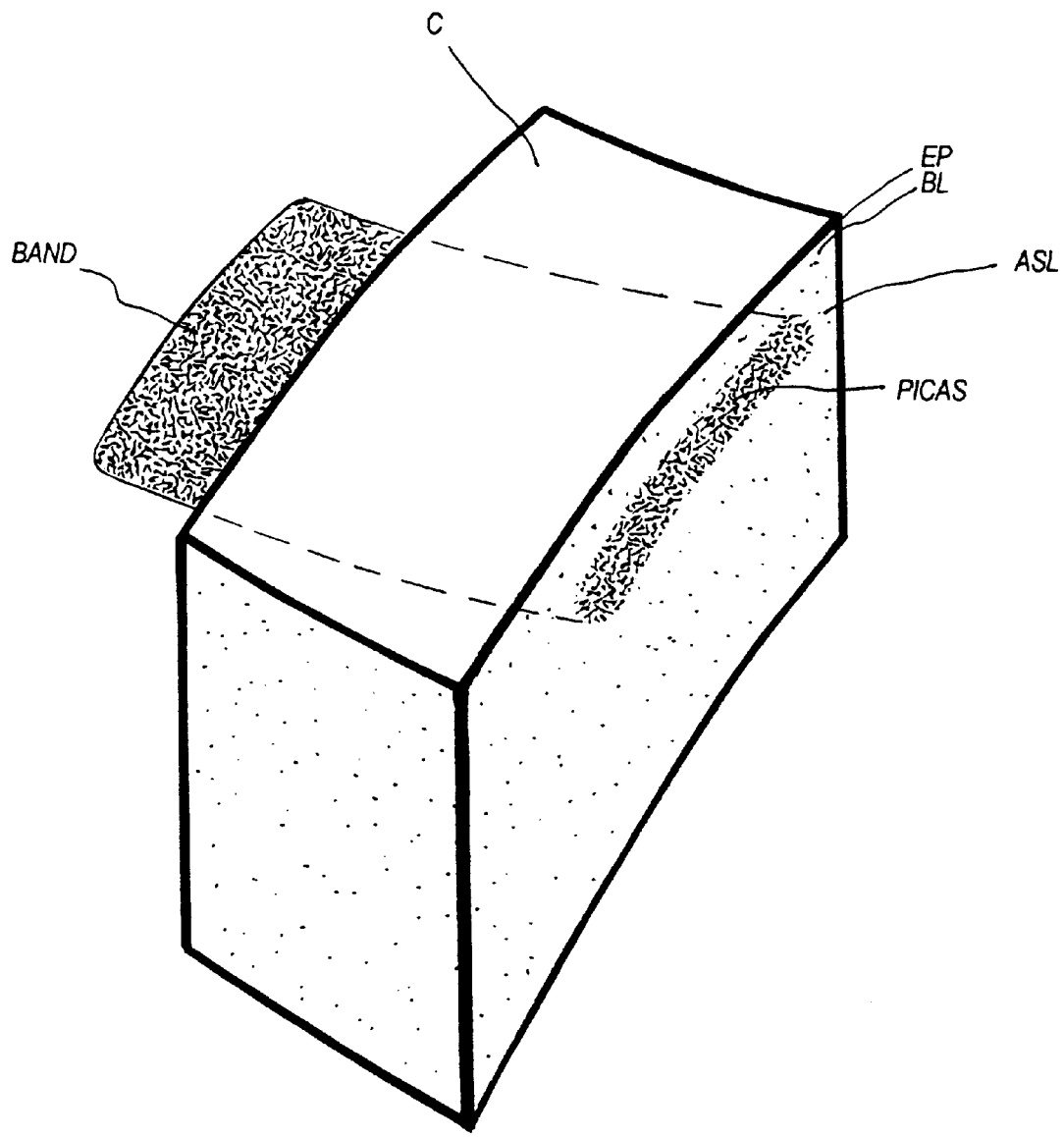
FIG. 12F depicts a portion of the 360° band or photo-intercalated region that results from the technique of the invention of FIGS. 12B–12D that can maintain the prolate corneal shape of FIG. 9.

FIG. 12F depicts a portion of the BAND that is created in 360° around the cornea comprising the photo-intercalated or PICAS welded region.

Of particular interest to the invention, the TAOS technique for the first time allows a subsurface "weld" or other above-physiologic thermal "effect" (i.e., any other photon-tissue interaction or modality) to be created in the cornea wherein the resultant thermal effect extends within a relatively thin subsurface plane or layer. This aspect of the technique contrast it with the prior art laser-tissue interactions in the cornea C wherein thermal effects always extend along the path of beam propagation which thus creates cylindrical-shaped or tapered irradiated volume. In the TAOS technique, throughout the duration of both cyro-wave propagation and photon energy propagation, the lens-prosthesis 100 is wetted against the anterior surface of the cornea and prevents upward disruption of the epithelium. At the same time, the lens-prosthesis 100 maintains the tear film TF at a physiologic thickness. This is to be contrasted with situations in which a cornea is left uncovered and the tear film may be intact or entirely evaporated prior to treatment, which will substantially alter the effects of photonic energy delivery.

It should be appreciated that the technique of the invention can be generalized to other tissues where subsurface photo-microwelding is desired while at the same time maintaining surface layers at or near physiologic temperatures.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. For example, it should be appreciated that the TAOS technique and M-alpha system may prove effective for certain types of photo-microwelding without the use of a lens-prosthesis intraoperatively. It should be appreciated that eye-tracking systems known in the art may be may included in the system. Further variations will be apparent to one skilled in the art in light of this disclosure and are intended to fall within the scope of the appended claims.

What is claimed is:

1. A technique for creating a shallow-plane weld-type lesion in a band within corneal lamellae for making the cornea slightly prolate in shape, comprising:

fitting a prolate-shaped lens-prosthesis over a patient's cornea thereby making the corneal shape slightly prolate;

delivering a dose of cryo-spray source toward the lens-prosthesis and cornea thereby causing a cyro-wave to commence propagation through the cornea;

delivering a dose of photonic energy at a particular fluence toward the lens-prosthesis and cornea thereby causing such photonic energy to be absorbed in the cornea;

wherein the propagation of photonic energy overtakes the cyro-wave and the particular fluence denatures molecules therein to create a weld-type lesion in front of the advancing cryo-wave thereby causing a weld-type lesion for maintaining the cornea in a slightly prolate shape.

2. A technique for creating a lesion within a patient's cornea for making the cornea slightly prolate in shape, comprising:

providing a transparent prosthesis with a base curvature that is steeper than the anterior curvature of the cornea;

delivering a dose of cryo-spray to the prosthesis fitted over the cornea thereby causing cooling to propagate through the prosthesis and cornea; and delivering a selected dose of photonic energy through the prosthesis to the cornea;

wherein the propagation of the photonic energy overtakes the propagation of the cooling; and wherein a fluence corresponding to the selected dose of the photonic energy denatures molecules in the lamellae of the cornea thereby creating the lesion.

3. The technique of claim 2, wherein the fluence creates the lesion within the corneal lamellae.

4. The technique of claim 2, wherein the fluence creates the lesion substantially in the anterior lamellae of the cornea.

5. The technique of claim 2, wherein the fluence creates the lesion in a band extending substantially 360° about a visual axis of the cornea.

6. The technique of claim 2, wherein the lesion extends in a substantially 360° band and thereby maintains the cornea in the slightly prolate shape.

7. The technique of claim 2, wherein the creation of the lesion maintains the cornea in a substantially steeper curvature than the pre-treatment curvature.

8. The technique of claim 2, wherein the creation of the lesion maintains the cornea substantially in a curvature similar to the base curvature of the prosthesis.

9. The technique of claim 2, wherein the delivering of the dose of cryo-spray alters the absorption coefficient of the corneal lamellae.

10. The technique of claim 2, wherein the delivering the dose of cryo-spray substantially prevents elevation of temperature in the epithelial layers of the cornea to ablative levels.

11. The technique of claim 2, further including maintaining the prosthesis over the cornea for 12 to 72 hours.

12. The technique of claim 2, further comprising repeating the technique as a maintenance therapy to steepen curvature of the cornea.

13. The technique of claim 2, wherein the lesion is created to a maximum depth of 150 microns in the cornea.

14. The technique of claim 2, wherein the lesion is created to a maximum depth of 15% of a thickness of the cornea.

15. The technique of claim 2, wherein a duration of the selected dose of photonic energy is no more than 300 ms.

16. A technique for altering the curvature of a patient's cornea, comprising:

fitting a prosthesis over the cornea with a base curvature that is steeper than the anterior curvature of the cornea in a paracentral zone;

at a first time delivering a coolant to the prosthesis thereby causing cooling to propagate through the cornea; and at a second time delivering a selected dose of photonic energy through the prosthesis to the cornea;

wherein a fluence corresponding to the selected dose of photonic energy causes formation of a lesion in the anterior lamellae of the cornea which in combination with the prosthesis causes an alteration in the curvature of the cornea.

17. The technique of claim 16, wherein the interval between the first time and the second time is in a range of 0.1 ms to 500 ms.

18. A method for altering the curvature of a patient's cornea, comprising:

fitting a prosthesis over the cornea wherein the base curvature of the prosthesis is steeper than the anterior corneal curvature in a paracentral zone;

delivering a selected dose of photonic energy through the prosthesis to the cornea in a band extending substantially 360° about the cornea;

wherein a fluence corresponding to the selected dose of photonic energy causes denaturation of proteins in the anterior lamellae of the cornea; and maintaining the prosthesis on the cornea for 12 to 72 hours during which the denatured proteins substantially form a weld-like lesion in the anterior lamellae thereby in combination with the prosthesis causing a maintainable alteration in curvature of the cornea.

* * * * *